Figure 1:
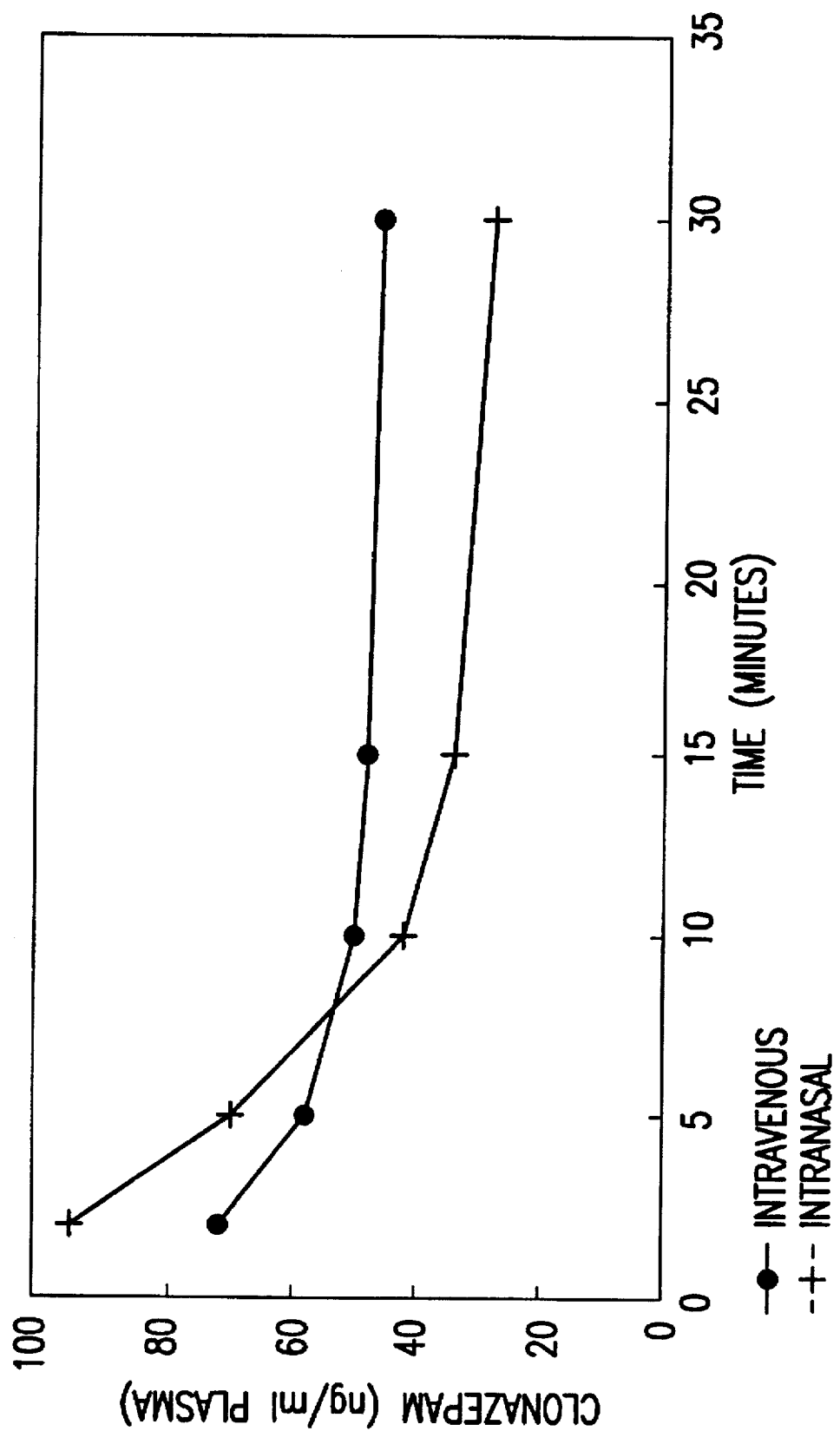

United States Patent [19]
Bechgaard et al.

[11] Patent Number: 5,693,608
[45] Date of Patent: Dec. 2, 1997

[54] METHOD OF ADMINISTERING A BIOLOGICALLY ACTIVE SUBSTANCE

[75] Inventors: Erik Bechgaard, Hellerup, Denmark; Sveinbjorn Gizurarson, Keflavik, Iceland; Rolf Kuhlman Hjortkjær, Humlebær, Denmark

[73] Assignee: Bechgaard International Research and Development A/S, Hellerup, Denmark

[21] Appl. No.: 395,838

[22] Filed: Feb. 28, 1995

Related U.S. Application Data

[63] Continuation of Ser. No. 151,802, Nov. 15, 1993, Pat. No. 5,428,006, which is a continuation of Ser. No. 71,604, Jun. 4, 1993, abandoned, which is a continuation of Ser. No. 870,893, Apr. 20, 1992, abandoned, which is a division of Ser. No. 696,564, May 8, 1991, abandoned.

[30] Foreign Application Priority Data

May 10, 1990 [DK] Denmark ................... 1170/90
Aug. 30, 1990 [DK] Denmark ................... 2075/90

[51] Int. Cl.$^6$ .................. A61K 38/00; A01N 37/18; C07K 5/00; C07K 7/00
[52] U.S. Cl. .................. 514/2; 514/4; 530/300
[58] Field of Search .................. 514/2, 4; 530/307, 530/311, 313, 300

[56] References Cited

U.S. PATENT DOCUMENTS

| | | | |
|---|---|---|---|
| 4,153,689 | 5/1979 | Hirai et al. | 424/178 |
| 4,524,075 | 6/1985 | Oduro-Yeboah | 514/451 |
| 4,547,572 | 10/1985 | Fenyvesi et al. | 536/103 |
| 4,613,500 | 9/1986 | Suzuki et al. | 429/85 |
| 5,428,006 | 6/1995 | Bechgaard et al. | 514/3 |

FOREIGN PATENT DOCUMENTS

| | | | |
|---|---|---|---|
| 43499/89 | 3/1990 | Australia | A61K 31/55 |
| 0095897 | 12/1983 | European Pat. Off. | A61K 9/06 |
| 119420 | 9/1984 | European Pat. Off. | C08B 37/16 |
| 1554157 | 10/1979 | United Kingdom | A61K 37/26 |
| 9002737 | 3/1990 | WIPO | C07D 233/16 |

OTHER PUBLICATIONS

Lau et al., *Int'l J of Pharm*, vol. 54, 1989 pp. 171-174.

*Primary Examiner*—Avis M. Davenport
*Attorney, Agent, or Firm*—Evenson, McKeown, Edwards & Lenahan P.L.L.C.

[57] ABSTRACT

A method for administering a therapeutically effective amount of a biologically active substance to the circulatory system of a mammal including administering a pharmaceutical composition having a total volume of 1-1000 µl to a nasal mucosal membrane of the mammal, the pharmaceutical composition including the therapeutically effective amount of the biologically active substance dissolved or suspended in a volume of 1-1000 µl of an n-ethylene glycol containing vehicle including at least one n-ethylene glycol represented by the formula:

$$H(OCH_2CH_2)_pOH$$

wherein p is from 1 to 8, so that upon administration of the pharmaceutical composition to the nasal mucosal membrane, absorption of the biologically active substance through the mucosal membrane and into the blood stream of the mammal rapidly takes place and thereby allows the biologically active substance to exert its therapeutic effect.

30 Claims, 16 Drawing Sheets

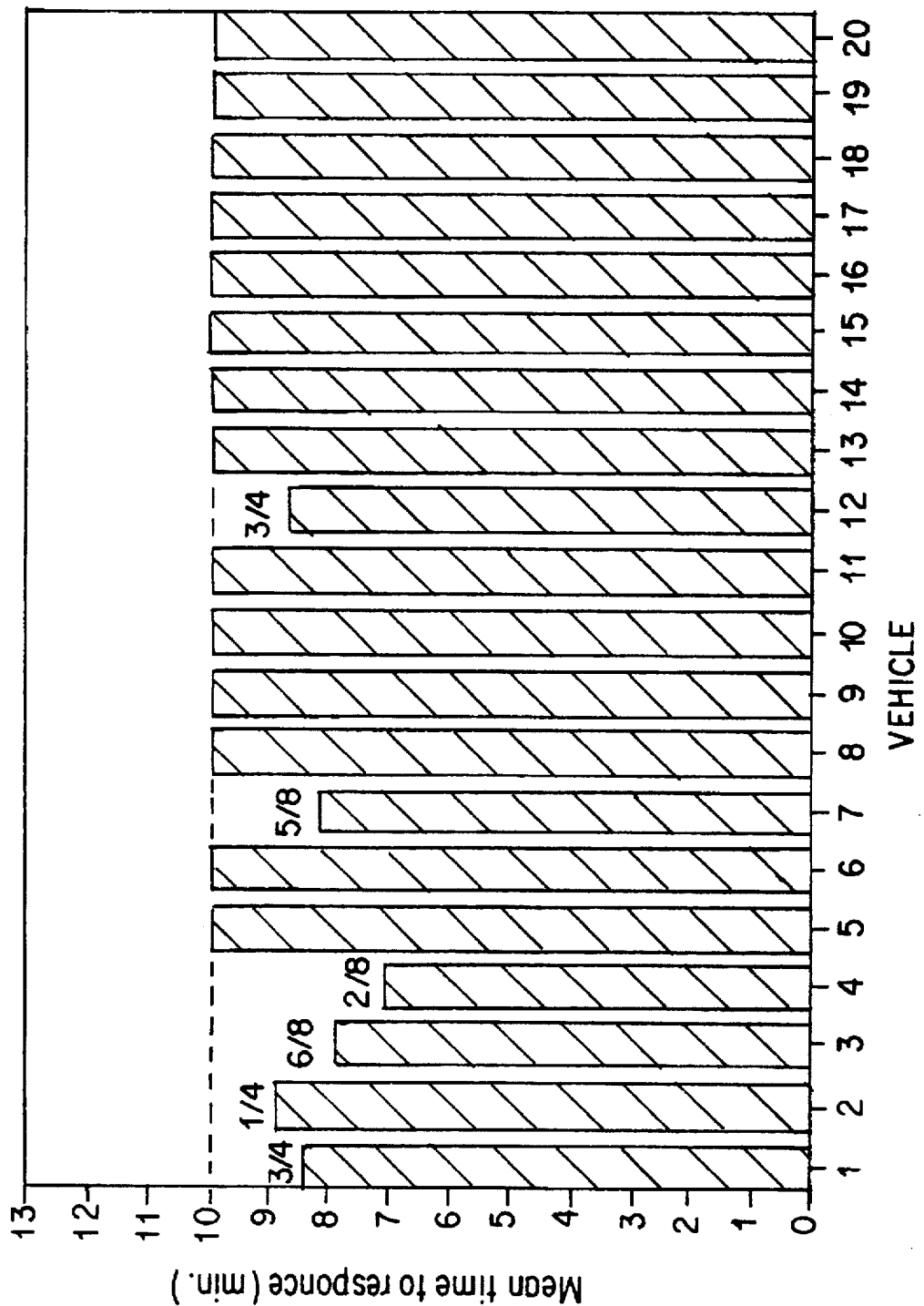

5,693,608

METHOD OF ADMINISTERING A BIOLOGICALLY ACTIVE SUBSTANCE

This is a continuation of application Ser. No. 08/151,802, filed Nov. 15, 1993 now U.S. Pat. No. 5,428,006 which is a continuation of Ser. No. 08/071,604, filed Jun. 4, 1993 now abandoned, which is a continuation of Ser. No. 07/870,893, filed Apr. 20, 1992 now abandoned, which is a divisional of Ser. No. 07/696,564, filed May 8, 1991 now abandoned.

The present invention relates to pharmaceutical compositions for administration of a biologically active substance to a mammal via a mucosal membrane.

The administration by injection (intravenous, intramuscular and subcutaneous) of biologically active substances is normally regarded as the most convenient way of administration when the purpose is to achieve a rapid and strong systemic effect, e.g. within 3–5 minutes, and when the active substance is not absorbed or is inactivated in the gastrointestinal tract or by first-pass hepatic metabolism. However, the administration by injection presents a range of disadvantages. Thus it requires the use of sterile syringes and may cause pains and irritations, particularly in the case of repeated injections, including the risk of infection. Besides, injections cannot be administered by untrained persons.

Intranasal administration is currently receiving special interest, attempting to avoid the inconveniences caused by the direct invasion into the organism in connection with parenteral administration. Furthermore, this route of administration may conveniently be used as an alternative to parenteral injection, when a rapid onset of effect is needed, and it can be performed by an untrained person.

In order to be an attractive alternative to injection, intranasal administration should offer a similar relation of dosis to plasma concentration and should not cause any considerable pain or irritation to the patient nor any irreversible damage or irritation to the nasal mucosa. However, in the case of treatment of acute health threatening indications, a relatively high local irritation to the mucosa may be acceptable.

In nasal administration, the biologically active substance must be applied to the mucosa in such a condition that it is able to penetrate or be absorbed through the mucosa. In order to penetrate the mucus the vehicle must be biocompatible with mucus and hence have a certain degree of hydrophilicity. However, the vehicle should preferably also posses lipophilic properties in order to dissolve a physiologically active amount of certain biologically active substances.

The extensive network of blood capillaries under the nasal mucosa is particularly suited to provide a rapid and effective systemic absorption of drugs. Moreover, the nasal epithelial membrane consists of practically a single layer of epithelial cells (pseudostratified epithelium) and it is therefore more suited for drug administration than other mucosal surfaces having squamous epithelial layers, such as the mouth, vagina, etc. These surfaces, however, are also suited for the application of biologically active substances using the drug delivery system according to the invention.

The effective nasal absorption is considered very small if the biologically active substances is not available in water-soluble form (Proctor, 1985). This statement puts severe limitations on the use of the biologically active substances, which should be water soluble and stable in aqueous solutions.

A large number of biologically active substances, including drugs (such as benzodiazepines), vitamins and vaccines, have a limited degree of water-solubility and very often it is not possible to dissolve a clinically relevant amount in the relatively small volume which may be applied for intranasal administration.

For liquid compositions it is essential that an effective amount of the biologically active substance(s) can be dissolved in a volume of less than about 300 µl. A larger volume can be disagreeable to the patient and will evidently drain out anteriorly through the nostrils or posteriorly toward the pharynx. The result is that a part of the active substance is lost from he absorption site and that in practice it will be impossible reproducibly to administer a correct dose. The volume for human adults is preferably from about 1 µl to about 1000 µl and more preferably from about 50 µl to about 150 µl per nostril.

The mucosal epithelium in the nasal cavity is covered with many hair-like cilia being an important defense mechanism for the mammal by against inhaled dust, allergens and microorganisms. The normal half-time for non-absorbed substances administered to the nasal cavity is about 15 minutes due to the mucociliary clearance removing foreign particles and excess mucus toward the pharynx. For this reason it is preferred that the absorption occurs rapidly and preferably within 1 to 20 minutes.

A variety of vehicle systems for the nasal delivery of biologically active substances has been developed. Up to date the literature has suggested that uptake of biologically active substances from the nasal mucosa may be made possible by incorporation into the formulation of a special vehicle system or by the addition of certain absorption enhancing agents.

Lau and Slattery (1989) studied the absorption characteristics of diazepam and lorazepam following intranasal administration for the treatment of status epilepticus. In order to solubilize these drugs, a non-ionic surfactant, polyoxyethylated castor oil, was selected as the least irritating out of several solvents studied including polyethyleneglycol 400. Diazepam absorption was 84 and 72%, respectively, in two adults measured over a period of 60 hours. However, the peak concentration was not observed until 1.4 hours after the nasal administration and was only about 27% with reference to i.v. administration, which indicate that most of the absorption had probably taken place after the test substance was cleared down to pharynx and swallowed. Similar results were obtained for lorazepam giving an even longer time to peak (2.3 hours). The authors conclude that the intranasal route of administration had limited potential for the acute treatment of epileptic seizures.

Wilton et al. (1988) attempted to administer midazolam to 45 children for achieving preanaesthetic sedation. The volumes used were very impractical and exceeded the maximal volume required for efficient administration resulting in coughing and sneezing with expulsion of part of the dose. The paper does not describe the aqueous vehicle system used.

International Patent Publication No. WO 86/04233 discloses a pharmaceutical composition wherein the drug (e.g. diazepam) is dissolved in a mixture of propellant and co-solvent e.g. glycerolphosphatide. This composition requires a pressurized system and at least one halogenated hydrocarbon aerosol propellant.

Morimoto et al. (1987) have studied a gel preparation for nasal application in rats of nifedipine containing the gelling agent carbopol (polyacrylic acid) in polyethyleneglycol 400 (PEG 400), for achieving prolonged action and high bioavailability of the drug. A mixture of equal amounts of carbopol and PEG 400 was preferred. It was shown that nasal application provided higher bioavailability of nifedipine than after peroral administration, but the plasma peak concentration was not observed until after 30 minutes, and it was only ≦10% as compared with intravenous administration.

DK patent application no. 2586/87 discloses a pharmaceutical composition comprising an antiinflammatoric steroid, water and only 2 to 10 volume-percent propylene glycol, 10 to 25 volume-percent polyethyleneglycol 400 and 1 to 4 volume-percent Tween 20.

U.S. Pat. No. 4,153,689 discloses a principle for obtaining a stable aqueous solution of insulin intended for intranasal administration. It has a pH in the range from 2.5 to 4.7 and it contains from 0.1 to 20 weight percent of a stabilizing agent selected from the group consisting of (a) at least one non-ionic surface active agent with hydrophile-lipophile balance value in the range of 9 to 22, (b) a stabilizing agent selected from polyethylene glycoly's having a molecular weight in the range from 200 to 7500 and (c) mixtures of stabilizing agents mentioned in (a) and (b).

International Patent publication No. 90/02737 discloses nasal administration of benzodiazepine hypnotics in a pharmaceutically acceptable nasal carrier. The carrier may be a saline solution, an alcohol, a glycol, a glycol ether or a mixture thereof. There is no indication that the presence of a glycol or a glycol ether should be impart special advantages to the preparation, nor that the presence should be critical for the administration Other preparations for intranasal or sublingual administration are disclosed in U.S. Pat. No. 4,746,508 disclosing the uptake of e.g. insulin by using fusidic acid and derivatives as absorption promoters and in International Patent Publication No. WO 87/05210 disclosing a sublingual sprayable pharmaceutical preparation optionally comprising PEG and requiring ethanol, diglyceride and/or triglyceride of fatty acid and a pharmaceutically acceptable propellant gas.

The primary object of the invention is to provide a pharmaceutical composition for application of a biologically active substance via a mucosal membrane of a mammal which composition is capable of producing a high plasma concentration of the pharmaceutically active sustance nearly as rapid as by i.v. administration, without causing unacceptable damage to the mucosal membrane. This object is fulfilled with the composition of the invention The pharmaceutical preparation of he present invention is characterized in comprising from 0.1–30%, preferably 0.1–20%, more preferably 1–15% of one or more substance (s) selected of n-glycofurols represented by the formula I:

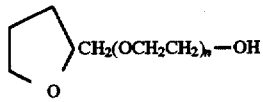

wherein n is an integer of 1 to 4, in an n-ethylene glycol represented by the formula II:

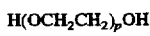

wherein p is an integer of 3–8 or in water or in a vegetable oil or in a mixture of water and/or n-ethylene glycol and/or vegetable oil.

According to a preferred aspect of the invention the preparation comprises tetraethylene glycol.

The pharmaceutical composition of the invention preferably comprises n-glycofurols wherein n is 1 or 2.

In accordance with a preferred aspect of the invention there is provided a pharmaceutical preparation comprising one or more n-glycofurols and one or more n-ethylene glycols.

The pharmaceutical composition of the invention may comprise a biologically active substance selected from the group consisting of Adrenal hormones, corticosteroids and derivatives such as ACTH and analogues, teracosactrin, alsactide, cortisone, cortisone acetate, hydrocortisone, hydrocortisone alcohol, hydrocortisone acetate, hydrocortisone hemisuccinate, prednisolone, prednisolone terbutate, 9-alpha-fluoroprednisolone, triamcinolone acetonide, dexamethasone phosphate, flunisolide, budesonide, toxicorol pivalate, etc.; Amino acids; Anorectics such as benzphetamine HCl, chlorphentermine HCl, etc. Anitbiotics such as tetracycline HCl, tyrothricin, cephalosporine, aminoglycosides, streptomycin, gentamycin, leucomycin, penicillin and derivatives, erythromycin, etc.; Anti-allergic agents; Anitbodies such as monoclonal or polyclonal antibodies against infectious diseases; Anti-cholinergic agents such as atropine base, etc.; Anti-depressants such as amitriptyline HCl, imipramine HCl, etc.; Anti-emetica such as neuroleptica, e.g. metopimazin, antihistamins e.g. thienylperazin or anti-emetica having a regulatory effect on the motility of the intestine such as domperidon; Anti-epileptica and anti-spasmolytica such as clonazepam, diazepam, nitrazepam, lorazepam etc.; Anti-histaminic and histaminic agents such as diphenhydramin HCl, chloropheniramine maleate, clemastine, histamine, prophenpyridamine maleate, chlorprophenpyridamine maleate, disodium cromoglycate, meclizine, etc. Anti-hypertensive agents such as clonidine HCl, etc.; Anti-inflammatory agents (enzymatic) such as chymotrypsin, bromelain seratiopeptidase, etc.; Anti-inflammatory agents (non-steroidal) such as acetaminophen, aspirin, aminopyrine, phenylbutazone, mefenamic acid, ibuprofen, diclofenac sodium, indomethacin, colchicine, probenocid, etc.; Anti-inflammatory agents (steroidal) such as hydrocortisone, prednisone, fluticasone, predonisolone, triamcinolone, triamcinolone acetonide, dexamethasone, betamehasone, beclomethasone, beclomethasone dipropionate, etc.; Anti-neoplastic agents such as actinomycin C, etc.; Anti-septics such as chlorhexidine HCl, hexylresorcinol, dequalinium cloride, ethacridine, etc.; Anti-tumor agents: Anti-tussive expectorant (asthmatic agents) such as sodium cromoglycate, codeine phosphate, isoprotereol HCl, etc.; Anti-viral and anti-cancer agents such as interferons (such as Alpha-2 interferon for treatment of common colds), phenyl-p-guanidino benzoate, enviroxime, etc.; Beta-adrenegic blocking agents such as propranolol HCl, etc.; Blood factors such as factor VII, factor VIII etc. Bone metabolism controlling agents such as vitamins $D_3$, active vitamine $D_3$, etc.; Bronchodilators such as clenbuterol HCl, bitolterol mesylate, etc.; Cardiotonics such as digitalis, digoxin, etc.; Cardiovascular regulatory hormones, drugs and derivatives such as bradykin antagonists, atrial natriuretic peptide and derivatives, hydralazine, angiotensin II antagonist, nitroglycerine, nifedipine, isosorbide dinitrate, propranolol, clofilium tosylate, etc.; Chemotherapeutic agents such as sulphathiazole, nitrofurazone, etc.; CNS-stimulants such as lidocaine, cocaine, etc.; Corticosteroids such as lacicortone, hydrocortisone, fluocinolone acetonide, triamcinolone acetonide, etc.; Diagnostic drugs such as phenolsulfonphthalein, dey T-1824, vital dyes, potassium ferrocyanide, secretin, pentagastrin, cerulein, etc.; Dopaminergic agents such as bromocriptine mesylate, etc.; Enzymes such as lysozyme chloride, dextranase, etc.; Gastrointenstinal hormones and derivatives such as secretin, substance P, etc.; Hypothalamus hormones and derivatives such as LHRH and analogues (such as nafarelin, buserelin, zolidex, etc.), enkephalins (DADLE, metkephamid, leucine enkephalin), TRH (thyrotropin releasing hormone), etc.;

Hypothensives; Local anesthitics such as benzocain, etc.; Migraine treatment substances such as dihydroergotamine, ergometrine, ergotamine, pizotizin, etc.; Narcotics, antagonists and analgetics such as buprenorphine, naloxone etc.; Pancreatic hormones and derivatives such as insulin (hexameric/dimeric/monomeric forms), glucagon, etc.; Parasympathomimetics such as nicotine, methacholine, etc.; Parasympatholytics such as scopolamine, atropine, ipratropium, etc.; Parcinson disease substances such as apomorphin etc.; Pituitary gland hormones and derivatives such as growth hormone (e.g. human), vasopressin and analogues (DDAVP, Lypressin), oxytocin and analogues, etc.; Prostaglandines such as PGA and derivatices, $PGE_1$ and derivatives, $PGE_2$ and derivatives, $PGF_1$ and derivatives, dinoprost trometamol, etc.; Protease inhibitors such as aprotinin, citrate, or $\alpha_1$-antitrypsin etc.; Sedatives such as alprazolam, bromazepam, brotizolam, camazepam, chlordiazepeoxide, clobazam, chlorazepic acid, clonazepam, clotiazepam, cloxazolam, delorazepam, diazepam, estazolam, ehtyl loflazepate, fludiazepam, flunitrazepam, flurazepam, flutazolam, halazepam, haloxazolam, ketazolam, loprazolam, lorazepam, lormetazepam, medazepam, midazolam, nimetazepam, nitrazepam, nordiazepam, oxazepam, oxazolam, pinazepam, prazepam, temazepam, tetrazepam, tofisopam, triazolam, etc.; Sex-hormones such as ethinyloestradiol, levonorgestrel, FSH, LH, LTH, estradiol-17-beta, progesterone, norethindrone, testosterone, etc.; Sympathomimetics such as ephedrine, epinephrine, phenylephrine, xylometazoline, tramazoline, dopamine, dobutamine, etc.; Throid gland hormones and derivatives such as calcitronins and synthetic modifications thereof etc.; Tranquillisers such as alprozolam, bromazepam, brotizolam, camazepam, chlordiazepeoxide, clobazam, chlorazepic acid, clonazepam, clotiazepam, cloxazolam, delorazepam, diazepam, estazolam, ethyl loflazepate, fludiazepam, flunitrazepam, flurazepam, flutazolam, halazepam, haloxazolam, ketazolam, loprazolam, lorazepam, lormetazepam, medazepam, midazolam, nimetazepam, nitrazepam, nordiazepam, oxazepam, oxazolam, pinazepam, prazepam, temazepam, tetrazepam, tofisopam, triazolam, etc.; Vaccines such as AIDS-vaccines, influenza virus, parainfluenza virus, measles, polio, rhinovirus type 13, respiratory syncytial virus etc.; Vasoconstrictors such as phenylephrine HCl, tetrahydrozoline HCl, naphazoline nitrate, oxymetazoline HCl, tramazoline HCl, etc.; Vasodilatros such as nitroglycerin, papaverine HCl, substance P, VIP (vasoactive intestinal peptide) etc; Vitamines such as vitamin-$B_{12}$, folic acid, or nicotinamide.

The composition of the invention comprises, according to a preferred aspect of the invention, a biologically active substance selected from the group consisting of Adrenal hormones, Corticosteriods and derivatives thereof, Amino acids, Anorectics, Antibiotics, Anti-allergic agents, Anticholinergic agents, Anti-depressants, Anti-dots, Anti-epileptics, Anti-histaminic and histaminic agents, Anti-hypersensiva, Anti-inflammatory agents (enzymatic, non steroidal and steroidal), Anti-neoplastic agents, Anti-septics, Anti-tumour agents, Anti-tussive expectorants (asthmatic agents), Anti-viral and anti-cancer agents, Beta-adrenergic blocking agents, Blood factors, Bone metabolism controlling agents, Bronchodilators, Cardiotonics, Cardiovascular regulatory hormones, drugs and derivatives, Chemotherapeutic agents, CNS-stimulants, Corticosteroids, Diagnostic drugs, Dopaminergic agents, Enzymes, Fibrinolytics, GABA antagonists, Gastrointestinal hormones and derivatives, Glutamate antagonists, Glycine antagonists, Hypothalamus hormones and derivatives, Hypothensives, Local anaesthetics, Migraine treatment substances, Narcotics, antagonists and analgetics, Pancreatic hormones and derivatives, Parasympathomimetics, Parasympatholytics, Pituitary gland hormones and derivatives, Prostaglandins, Sedatives, Sex-hormones, Spasmolytics, Sympathomimetics, Thyroid gland hormones and derivative, Tranquillises, Vaccines, Vasoconstrictors, Vasodilators, and Vitamins.

According to another aspect of the invention, the biologically active substance(s) is(are) selected from biologically active peptides which are digested in the gastrointestinal tract.

According to a more preferred aspect of the invention, the biologically active substance is selected from the group consisting of coagulation factors such as Factor VII, Factor VIII, Factor IX and derivatives and analogues thereof; agents controlling bone metabolism such as Vitamine $D_3$, active Vitamine $D_3$, calcitonin and derivatives and analogues thereof; hormones secreted by hypothalamus such as LHRH or analogues, e.g. nafarelin, buserelin or Zolidex, enkephalins such as DADLE, metkephamid or leucine enykephalin, and TPH and derivatives and analogues thereof; hormones secreted by pancreas such as insulin or glucagon and derivatives and analogues thereof; hormones secreted by the pituitary gland such as growth hormone, vasopressin or oxytocin and derivatives and analogues thereof, e.g. DDAVP or lypressin; sex-hormones such as ethinylestradiol, levonorgestrol, FSH, LH, LTH esynradiol-17$\beta$, progesterone, norethindrone or testosterone and derivatives and analogues thereof and tranquilizer such as alprazolam, bromazepam, brotizolam, camazepam, chlordiazepeoxide, clobazam, chlorazepic acid, clonazepam, clotiazepam, cloxazolam, delorazepam, diazepam, estazolam, ethyl loflazepate, fludiazepam, flunitrazepam, flurazepam, flutazolam, halazepam, haloxazolam, ketazolam, loprazolam, lorazepam, lormetazepam, medazepam, midazolam, nimetazepam, nitrazepam, nordiazepam, oxazepam, oxazolam, pinazepam, prazepam, temazepam, tetrazepam, tofisopam or triazolam and salts, salts and derivatives and analogues thereof.

According to another more preferred aspect of the invention, the biologically active substace selected from the group consisting of coagulation factors such as Factor VII, Factor VIII, Factor IX and derivatives and analogues thereof: agents controlling bone metabolism such as calcitonin and derivatives and analogues thereof: hormones secreted by hypothalamus such as LHRH or analogues, e.g. nafarelin, buserelin or Zolidex, enkephalins such as DADLE, metkephamid or leucine enkephalin hormones secreted by pancreas such as insulin or glucagon and derivatives and analogues thereof: hormones secreted by the pituitary gland such as growth hormone, vasopressin or oxytocin and derivatives and analogues thereof, e.g. DDAVP or lypressin sex-hormones such as FSH, LH or LTH and derivatives and analogues thereof.

The present invention is of particular importance when administering active substances being biologically active peptides which are digested in the gastrointestinal tract such as insulin, glucagon, growth hormone or insulin like growth factors or derivatives or analogues thereof.

In accordance with a more preferred aspect of the invention, the active substance is a pancreatic polypeptide hormone such as insulin and glucagon or a derivative or an analogue thereof.

In accordance with another preferred aspect of the invention, the active substance is selected among antiepileptica, spasmolytics and tranquilizers selected from the group of benzodiazepines such as clonazepam, diazepam, flunitrazepam, triazolamn, lorazepam, nitrazepam or mixtures thereof.

As has already been pointed out the active substance must be present in an effective amount within a total volume of not more than 1000 µl, preferably not more than 700 µl, a preferred dosage being 50–150 µl per nostril.

The active substance may be present in an amount of from 0.0001% to 50% of the total composition, preferably in an amount of from 0.001% to 20% e.g. in the case of benzodiazepins.

The pharmaceutical preparation of the invention may furthermore comprise nitric acid and/or nitrate in a concentration ranging from 0.0001 to 5%. Such component may act as a stabilizer for active substances such as clonazepam.

The pharmaceutical preparation of the invention may, in its broadest aspect, be considered as preparation comprising from 0.10–30% of one or more n-glycofurol represented by the above formula I wherein n is an integer of 1 to 4 and a carrier, in addition to the biologically active substance(s). Such carrier may comprise water and/or n-ethylene glycol and/or propylene glycol and/or vegetable oil and/or even powdery carrier of e.g. microspheres.

Furthermore, some pharmaceuticals preparations described herein outside of the 0.1–30% n-glycofural(s) range may be advantageous for special purposes, e.g. preparations comprising a very high proportions of glycofurols in the range of from 65–98% preferably a content of glycofurol in the range of 80–95%. Even a preparation comprising pure glycofurol and the pharmaceutically active ingredient may be advantageous for special purposes. The same applies for some preparations comprising a very high proportion of PEG e.g. pure 4EG or 3EG, even without the presence of glycofurol.

According to a further aspect of the invention the pharmaceutical preparation additionally comprises minor proportions of one or more compound(s) selected from the group consisting of surfactants, absorption promoters, water absorbing polymers, microspheres, oils, emulsions, liposomes, substances that inhibit enzymatic degradation, alcohols, organic solvents, water, hydrophobic agents, pH-controlling agents, preservatives and osmotic pressure controlling agents, cycylodextrines and propellants or mixtures thereof.

Preferably, the water absorbing polymers are polyethylene glycols having an average molecular weight ranging from 200 to 7500 or propylene glycol or mixtures thereof.

According to a preferred aspect of the invention the composition comprises more than 50% (w/w) of polyethylene glycol having an average molecular weight ranging from 200 to 1000.

The invention also relates to a method for treatment of a mammal with an effective amount of a biologically active substance wherein the dosage unit quantity of a biologically active substance is applied to a mucosal membrane of the mammal to be treated in a carrier which consists of from 0.1 to 30% of n-glycofurol represented by the formula I:

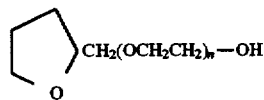

wherein n is 1 to 4, in n-ethylene glycol represented by the formula II:

wherein p is 3 to 8 or in water or in a vegetable oil or in a mixture of water and/or n-ethylene glycol and/or vegetable oil.

According to a further aspect the invention relates to the use of a pharmaceutical composition comprising a dosage unit quantity effective amount of a biologically active substance, from 1–30% n-glycofurols represented by the formula I:

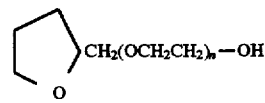

wherein n is 1 to 4, in n-ethylene glycols represented by the formula II:

wherein p is 3 to 8 or in water or in a vegetable oil or in a mixture of water and/or n-ethylene glycol and/or vegetable oil for application to a mucosal membrane.

The mucosal membrane to which the pharmaceutical preparation of the invention is administered may be any mucosal membrane of the mammal to which the biologically active substance is to be given, e.g. in the nose, vagina, eye, mouth, genital tract, lungs, gastrointestinal tract, or rectum, preferably the mucosa of the nose, mouth or vagina.

The pharmaceutical compositions of the invention may be administered in the form of a sublingual lozenge or troche or a buccal or nasal spray in the form of a solution, suspension or a powder, optionally together with various absorption enhancers or more preferred in the form of slightly viscous solution which is bioadhesive or optionally in the form of a suppository or vagitory.

According to a preferred aspect of the invention, the application is to the nasal mucosa, and the volume of the pharmaceutical composition is 1–1000 µl, preferably not more than 700 µl, say 50–150 µl per nostril, a most preferred exemplary dosage being 50 µl.

Also, 0.1–20% of the glycofurol(s) is preferred in the carrier composition, more preferably 1–15%.

The preferred use for the carrier compositions of the invention is in pharmaceutical preparations for systemic administration through the mucosa of the nose, mouth or vagina, most preferred through the mucosa of the nose, e.g. as a nasal spray.

The n-glycofurols of the formula I are considered to be a pharmaceutically acceptable carrier, especially a pharmaceutically acceptable carrier for nasal administration. According to another aspect of the invention n-glycofurols of the formula I are considered as an enhancer facilitating the uptake of biologically active substance through a mucosal membrane of a mammal, especially through the mucosa of the nose.

The present invention renders it possible to normalize e.g. the blood glucose level in subjects suffering from abnormalities in their sugar metabolism such as hypoglyycaemia or hyperglycaemia by giving gluycagon or insulin or an analogue or derivative thereof respectively, in a very easy and convenient manner.

Furthermore, the invention enables very convenient administration of bone metabolism controlling agents such as vitamin $D_3$ or Calcitonin and derivatives and analogues thereof; hormones secreted by hypothalamus such as LHRH such as nefarelin, buserelin or Zolidex and derivatives and analogues thereof hormones regulating the growth or mitogenic growth factors such as somatropin, IGF-1, IGF-2, FGF, PDGF, TGF, EGF, and derivatives and analogues thereof; protease inhibitors such as aprotinin, citrate, or $\alpha_1$-antitrypsin derivatives and analogues thereof; and cytochines such as IL-1 and IL-2, in order to normalize the blood level thereof in case of a deficiency.

Especially preferred for use in vehicle compositions according to the invention is glycofurol 75 (GF) which refers to commercially available solvents of polymers of the above formula I, wherein n is mainly 1 and 2. (Chemical Abstract Registration No. [9004 76-6]). Glycofurol 75 is a colourless liquid miscible with water, alcohols, such as methanol, ethanol, n-proypanol, glycerol and various oils in all proportions and has a b.p. about 155° C. GF is reported to cause irritation when used in compositions for parenteral administration undiluted form as reviewed by Spiegel and Nosewothy (1963). It has been reported to be non-toxic and non- when diluted in water (Spiegelberg et al., 1956).

The n-ethylene glycos used in accordance with the present invention may e.g. be triethylehe glycol (3EG), tetraethylene glycol (4EG), pentaethylene glycol (5EG), hexaethylene glycol (6EG), heptaethylene glycol (7EG), octaethylene glycol (8EG), nonaethylene glycol (9EG), decaethylene glycol (10EG), undecaethylene glycol (11EG), dodecaethylene glycol (12EG), tridecaethylene glycol (13EG) and tetradecaethylene glycol (17EG). The ethylene glycols may be used in the form of the single compounds or a mixture of two or more n-ethylene glycols, e.g. commercial products such as polyethylene glycol 200 (PEG 200) or polyethylene glycol 400 (PEG 400).

1EG to 14EG are colourless liquids miscible with water and alcohols in all proportions. PEG 200 is a commercially available mixture of ethylene glycols having an average molecular weight of about 200. The composition is shown in Table 1:

TABLE 1

| Composition of PEG 200 | |
|---|---|
| Monoethylene glycol | 0.1% |
| Diethylene glycol | 3.4% |
| Triethylene glycol | 21.2% |
| Tetraethylene glycol | 31.2% |
| Pentaethylene glycol | 24.4% |
| Hexaethylene glycol | 14.0% |
| Heptaethylene glycol | 5.4% |
| Octaethylene glycol | 0.3% |
| | 100.0% | nEG's and glycofuroles are available in various qualities. Especially preferred are highly purified qualities such as 4EG from Fluka-Chemie AG (Buchs, Switzerland, art. no.: 86660, 1990), abbreviated 4EGf.

The 4EG used in the preparations of the invention is preferably in a very pure form which improves the results.

The 4EG is preferably highly purified being >97% pure, the more preferred >98.5% pure giving the best results.

The delivery system according to the invention can be optimized e.g. with respect to bioadhesion, sprayability or viscosity. E.g. GF, in concentration of only 5%, has a surprisingly positive effect on the sprayability of e.g. 4EGf by reducing viscosity. Furthermore, the addition of 5% of GF is able to decrease the solidification temperature from about −10 to ≦−20 C. This is of importance where the formulation should be carried on persons or transported outdoor, ready for use.

The pharmaceutical composition of the invention may be used to treat animals such as domestic animals or pets or, preferably, human beings.

A special advantage in using the above vehicle system is that e.g. highly liypophilic substances such as the benzodiazepines as well as water soluble substances e.g. peptides and proteins such as the pancreatic hormones can be solubilized in clinically relevant dose for human subjects in only e.g. 25–300 µl of the vehicle. In aqueous solutions clinically relevant doses of diazepam and clonazepam will alternatively have to be dissolved in about 5000 ml and >10 ml, respectively.

The vehicle system according to the invention may be used in combination with various co-solvents, such as vegetable oil such as Miglyol® 840 (Dynamit Nobel Chemie, Troisdorf, W-Germany) or optionally hydrogenated or ethoxylated castor oil, which surprisingly increases the possibilities for designing a controlled release—formulation such as a diazepam formulation which avoids peak plasma concentrations.

The composition according to the invention may comprise one or more additional pharmaceutical exipients, such as: surfactants and absorption promoters having a hydrophillic-lipophilic balance from about 6 to 26 and ionic as well as non-ionic surfactants including polyoxyethylene alcohol ethers, bile salts and derivatives thereof, fusidic acid and derivatives thereof, oleic acid, lecithin, lysolecitins, or Tween 20 to 85; Water absorbing polymers, such as polyethyleneglycol 200 to 7500, polyvinylpyrrolidone, propyleneglycol, or polyacrylic acid, gelatine, cellulose and derivatives; Substances which inhibit enzymatic degradation, such as, citrate or aprotinin; Alcohols, such as, ethanol, glycerol, or benzylalcohol; Organic solvents, such as, ethylacetate, or benzylalcohol; Hydrophobic agents, such as vegetabile oil, e.g. soybean oil, peanut oil, coconut oil, corn oil, olive oil, sunflower oil, castor oil, Miglyol® 810/812/840 or mixtures thereof; pH-controlling agents, such as, nitric acid, phosphoric acid, or acetic acid, citrate: Preservatives and osmotic pressure controlling agents, such as glycerol, sodium chloride, methyl paraoxybenzoate, or benzoic acid; Powder compositions, such as, alfa-, beta- and gamma-cyclodextrines, cellulose and derivatives; Microspheres, liposomes and emulsions compositions, such as, starch, albumin, gelatine, or lecithins or lysoleciythins; Microencapsulated formulations; Proypellants such as butane; Water. The use of alcohols or propellants are not mandatory in the composition according to the invention.

Figure 2:
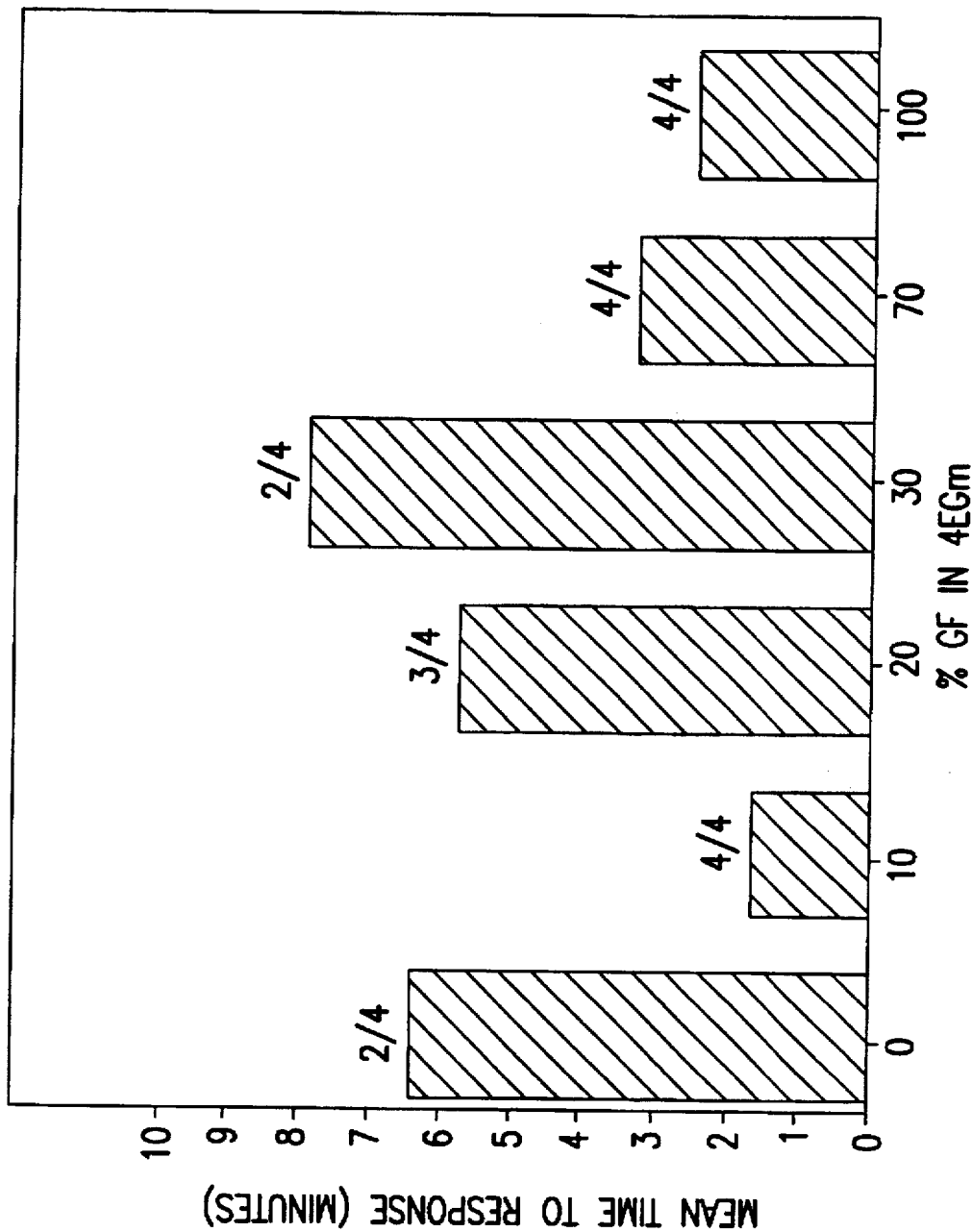
Figure 3:
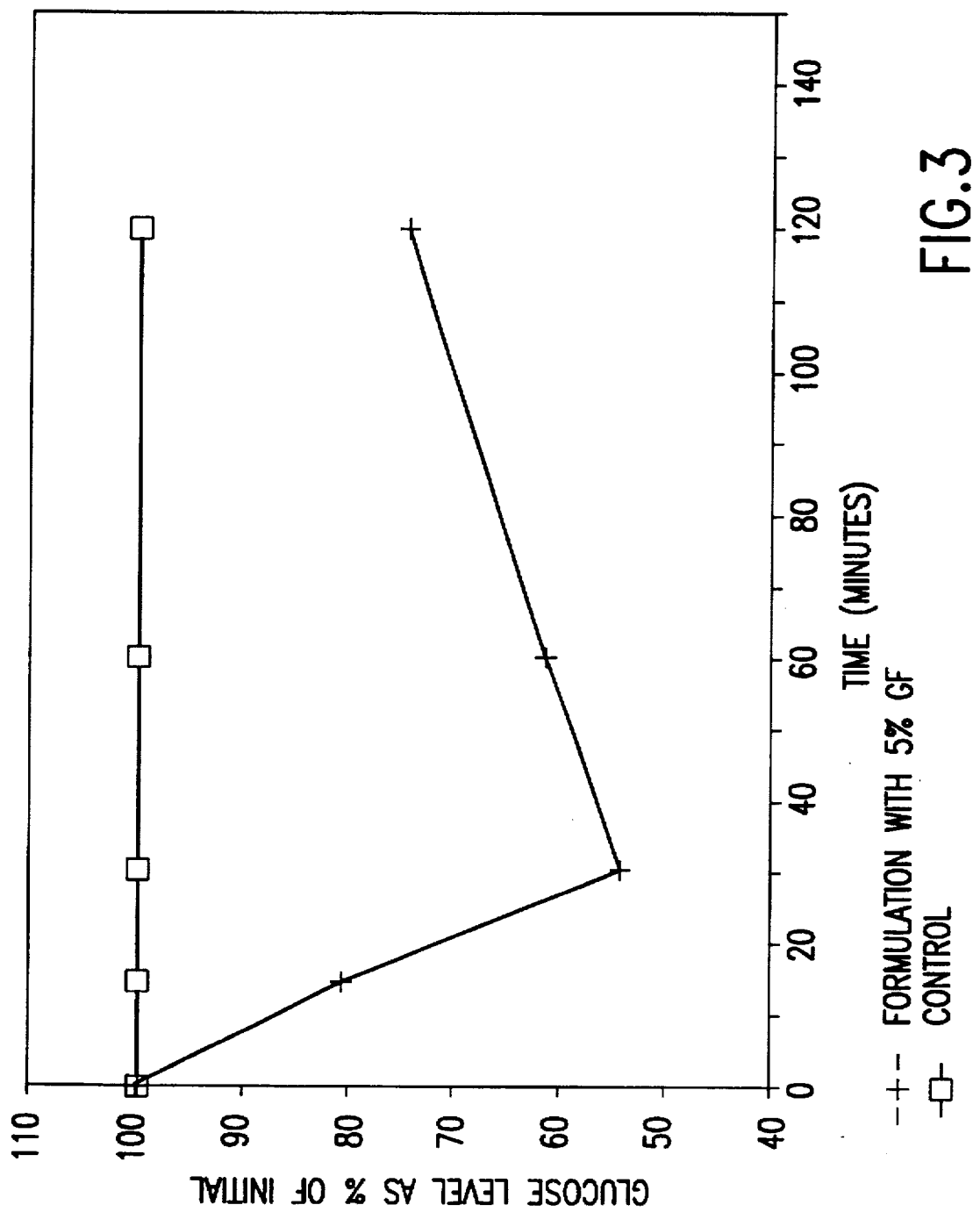
Figure 4:
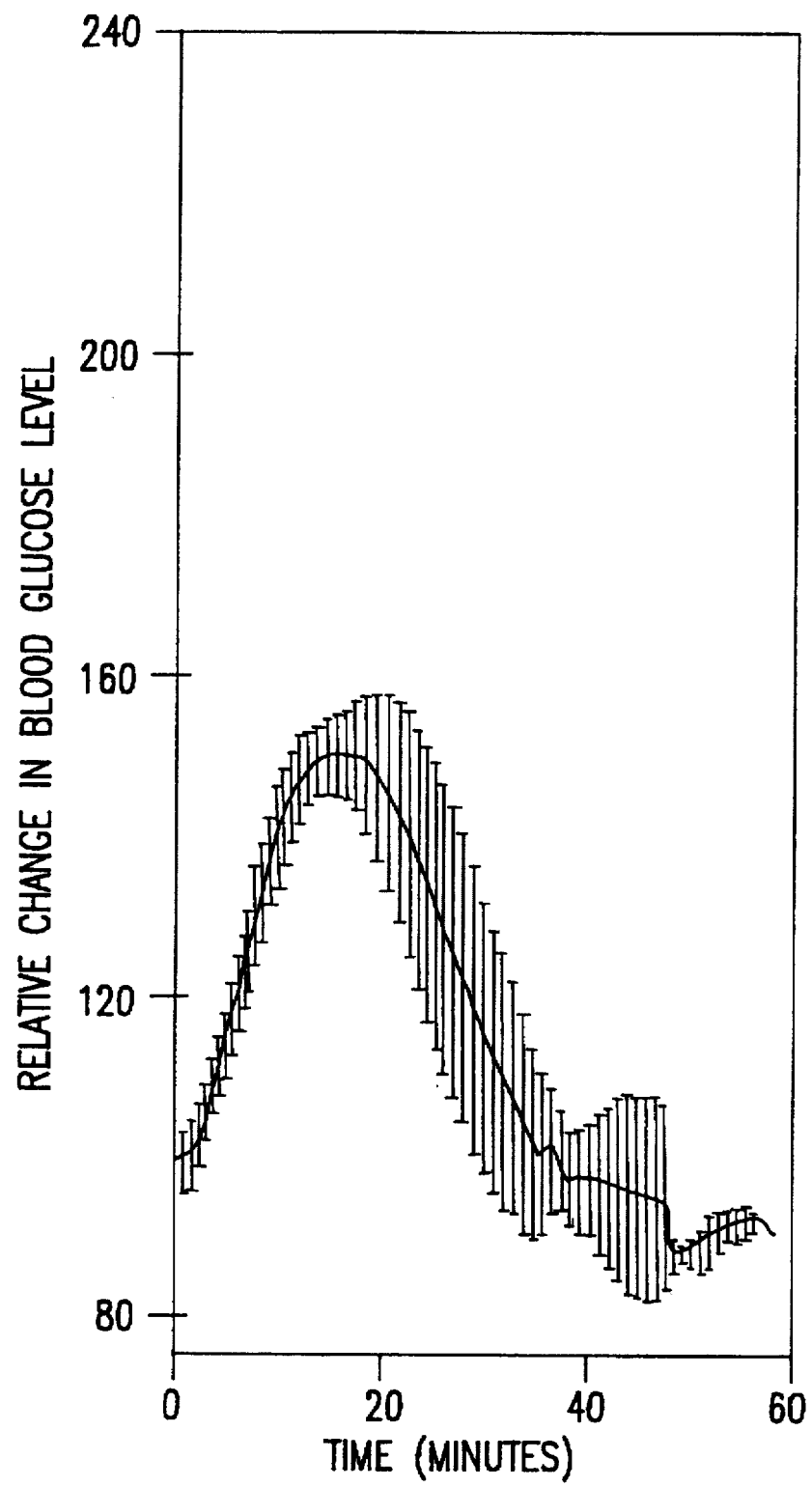
Figure 5:
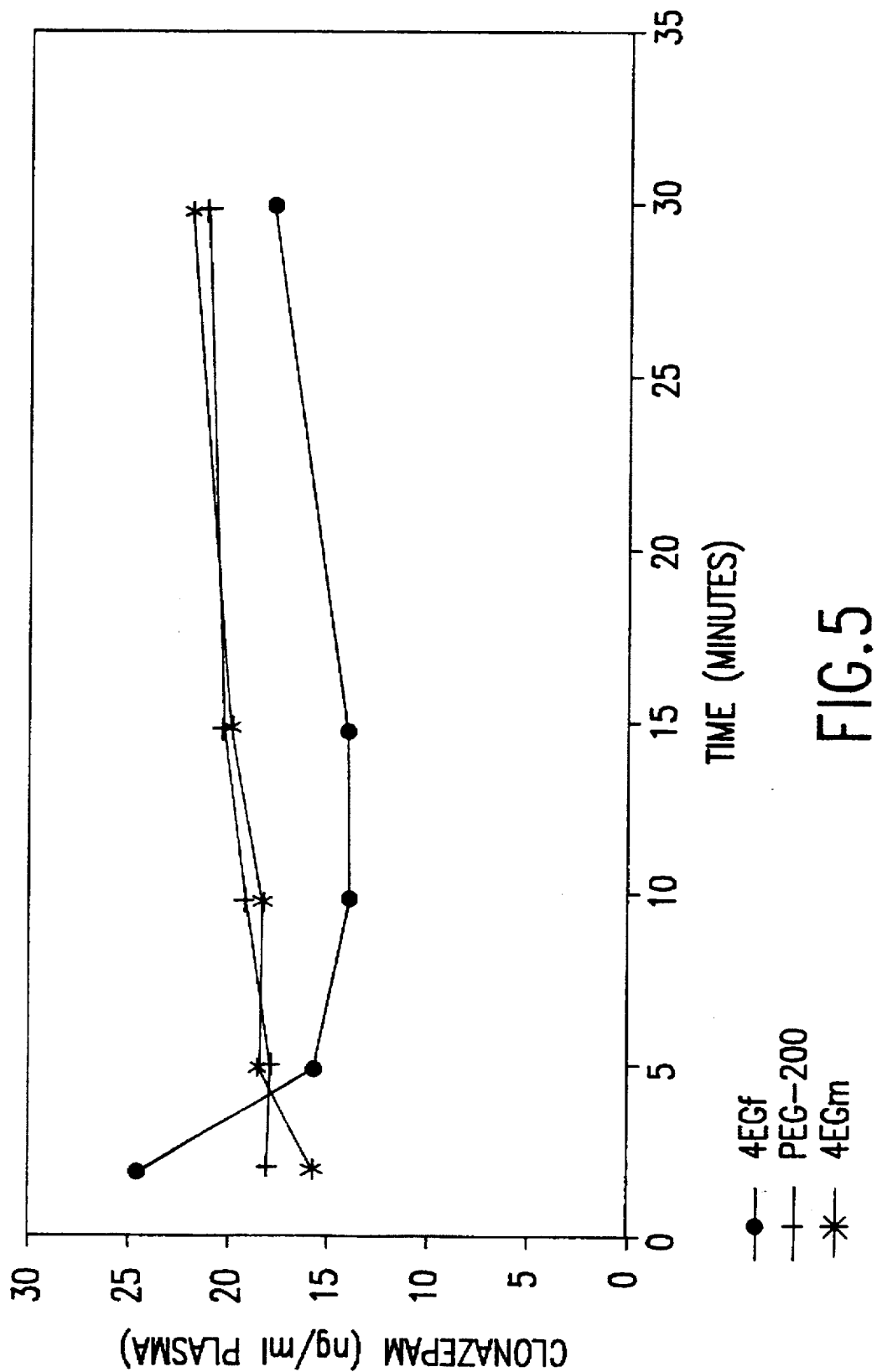
Figure 6:
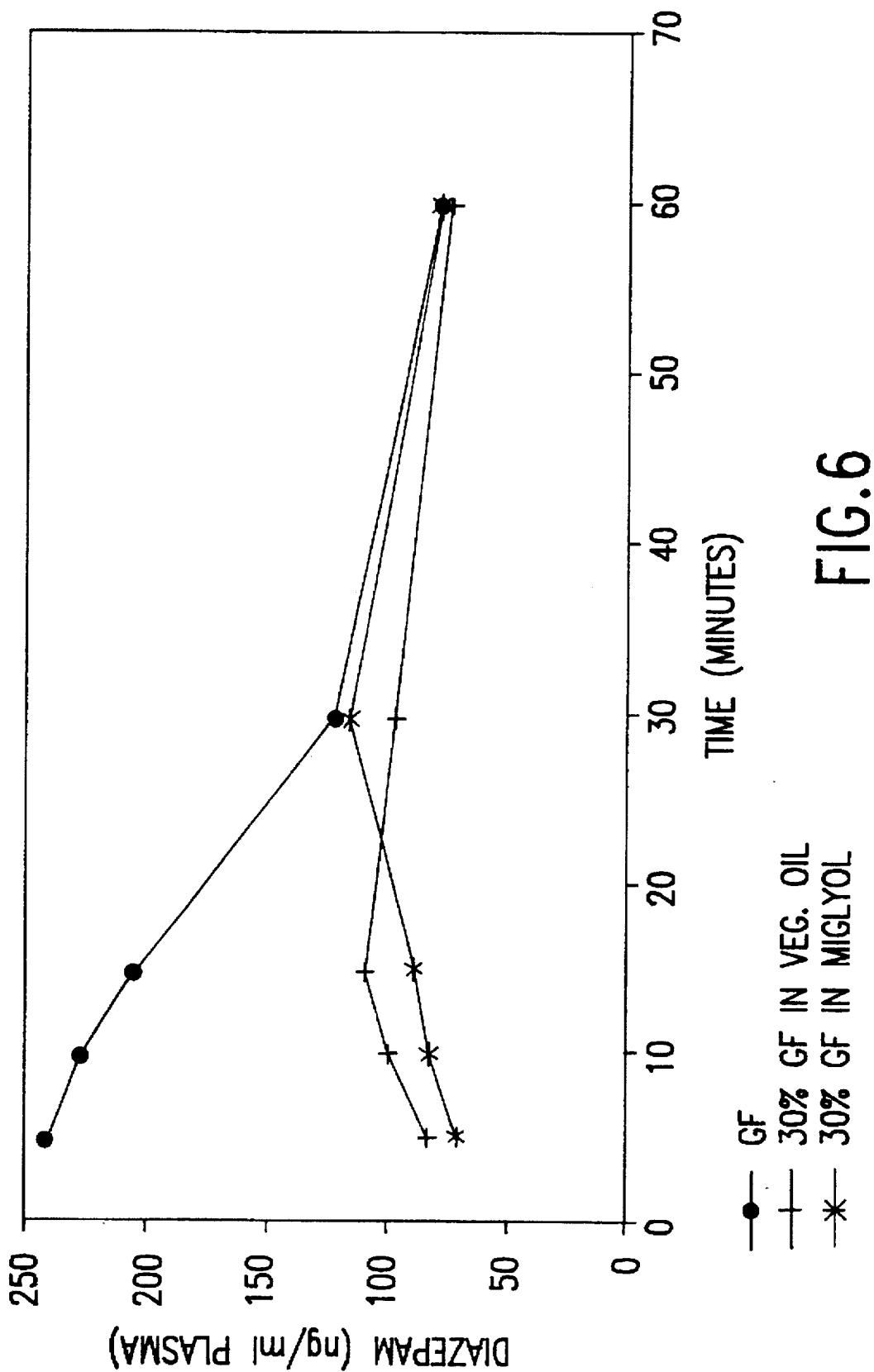
Figure 7:
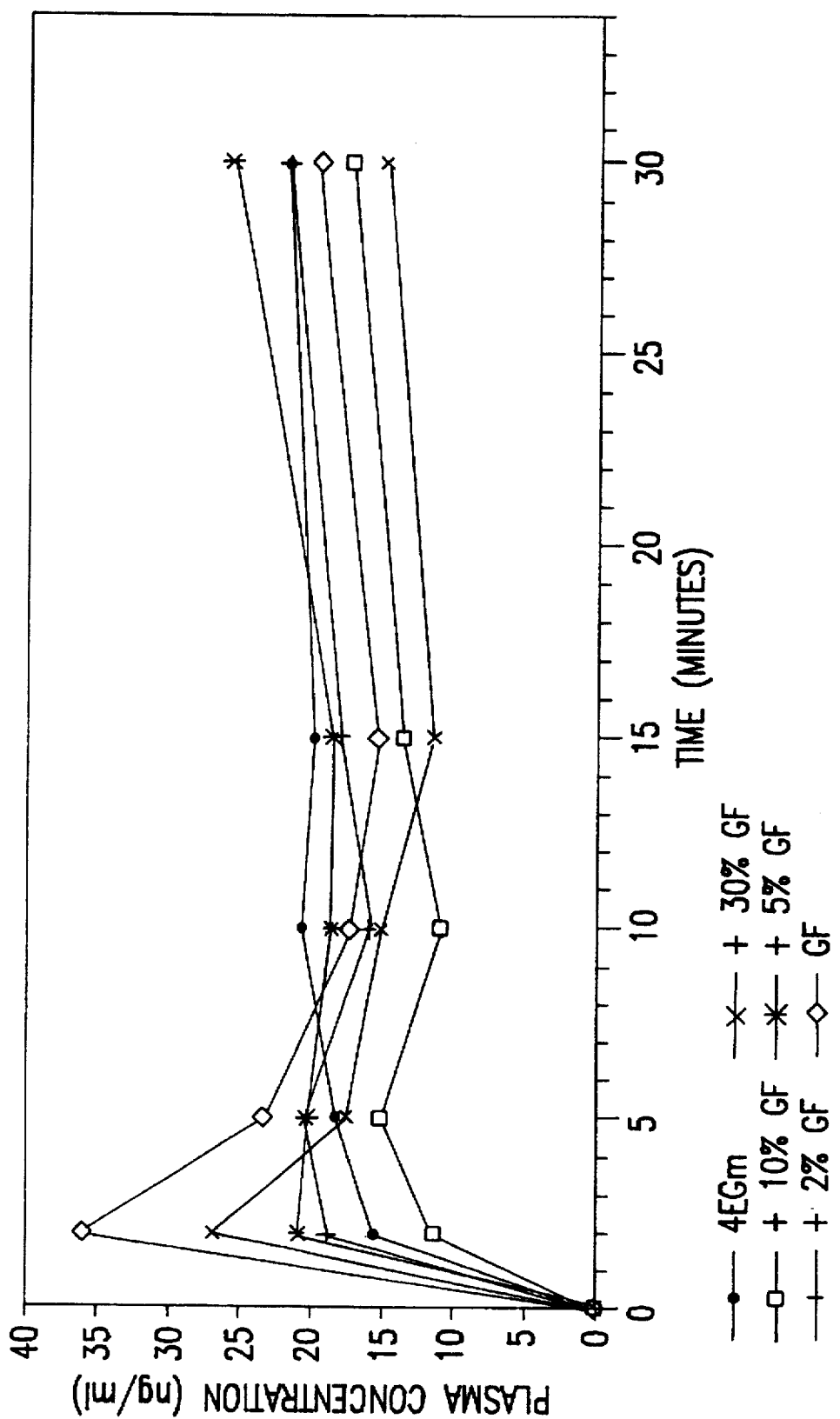
Figure 8:
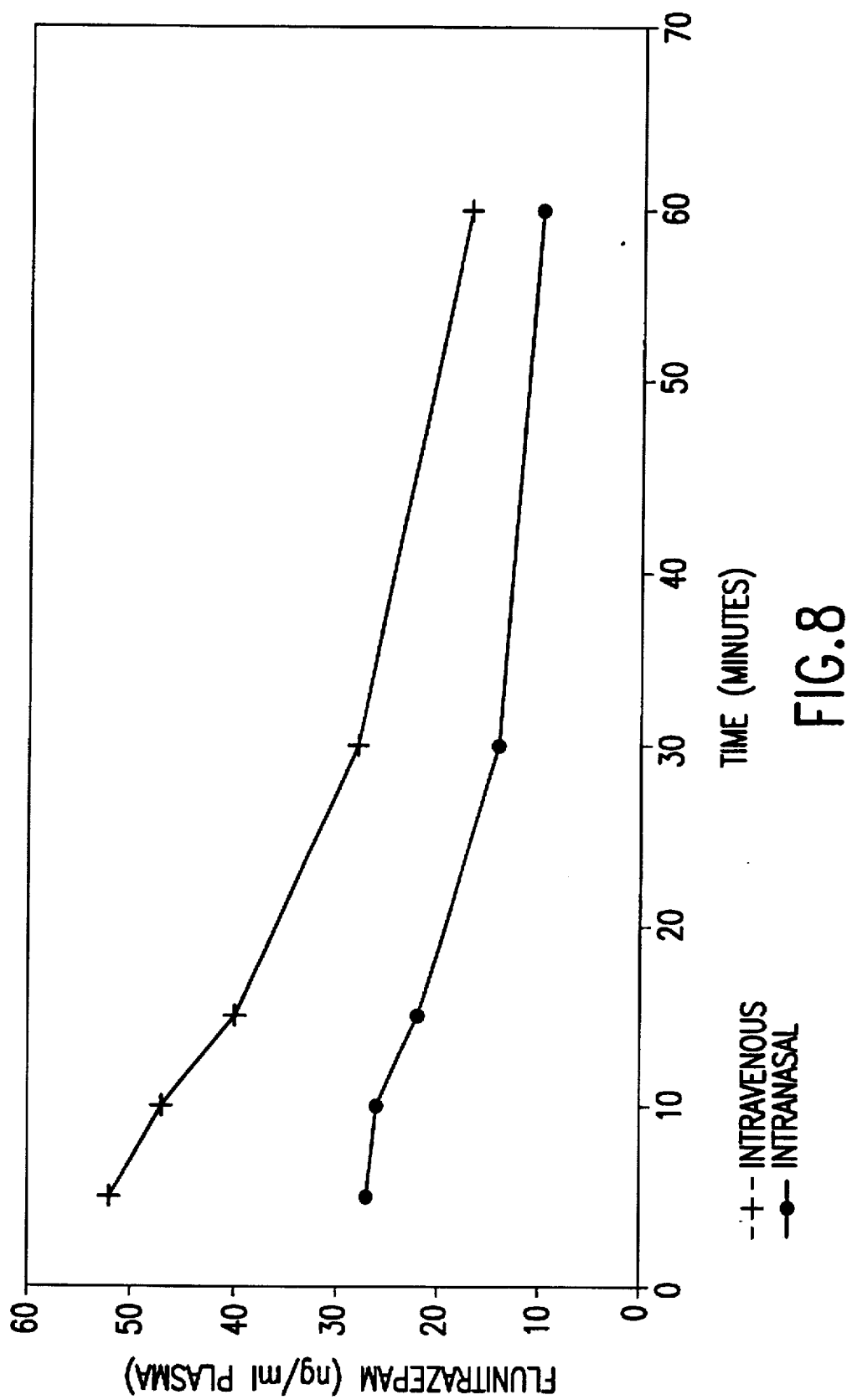
Figure 9:
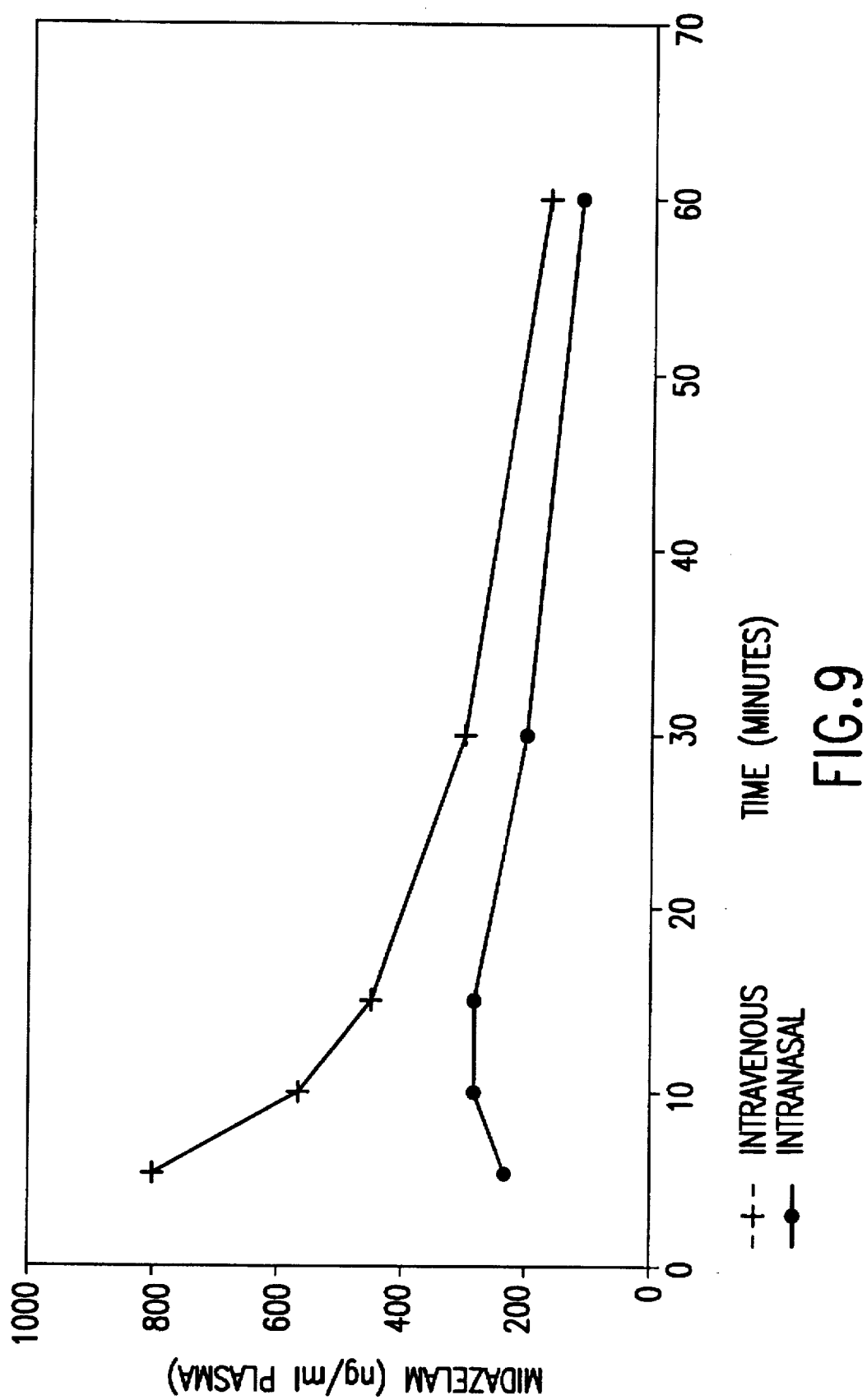
Figure 10:
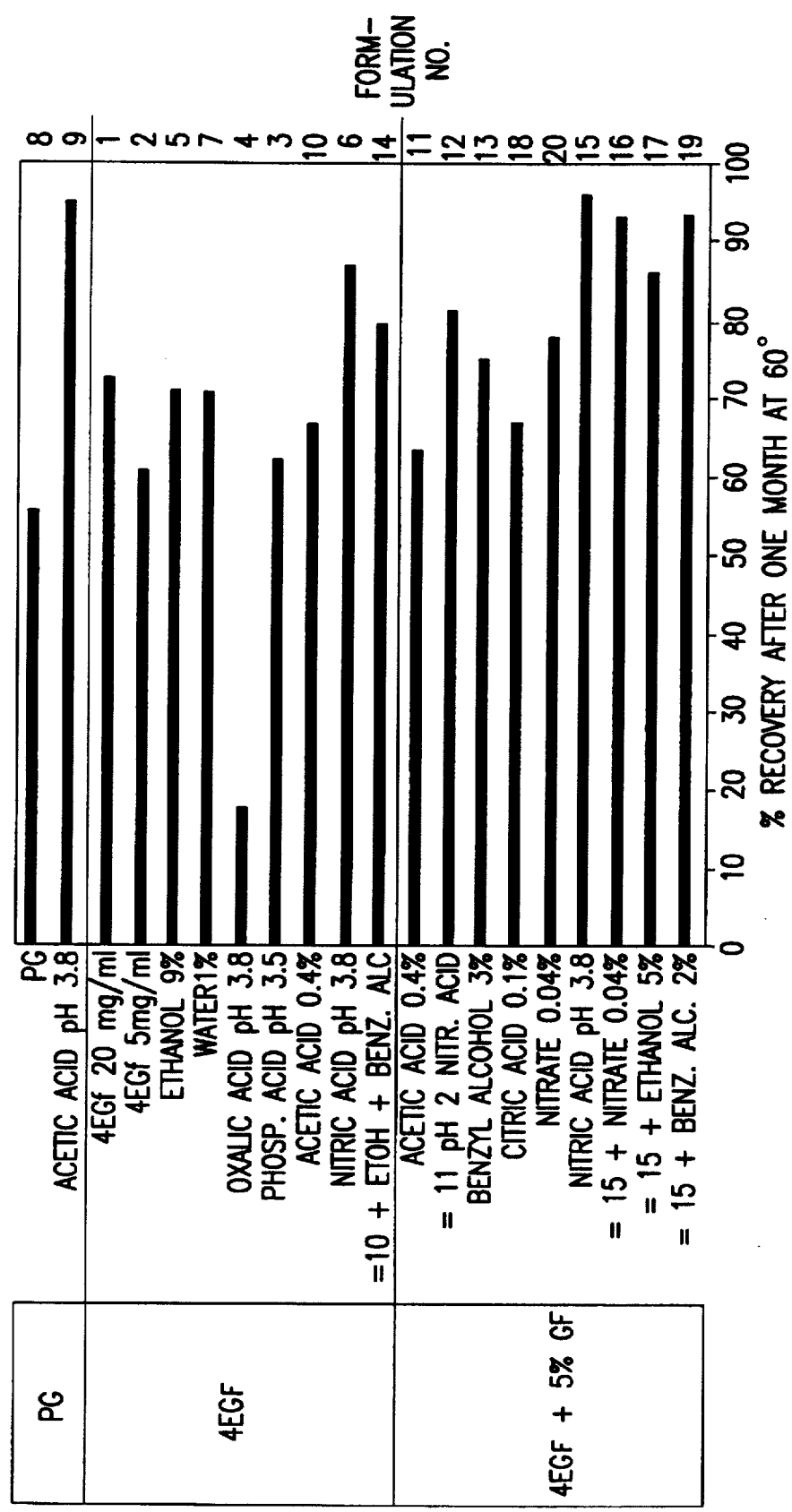
Figure 11:
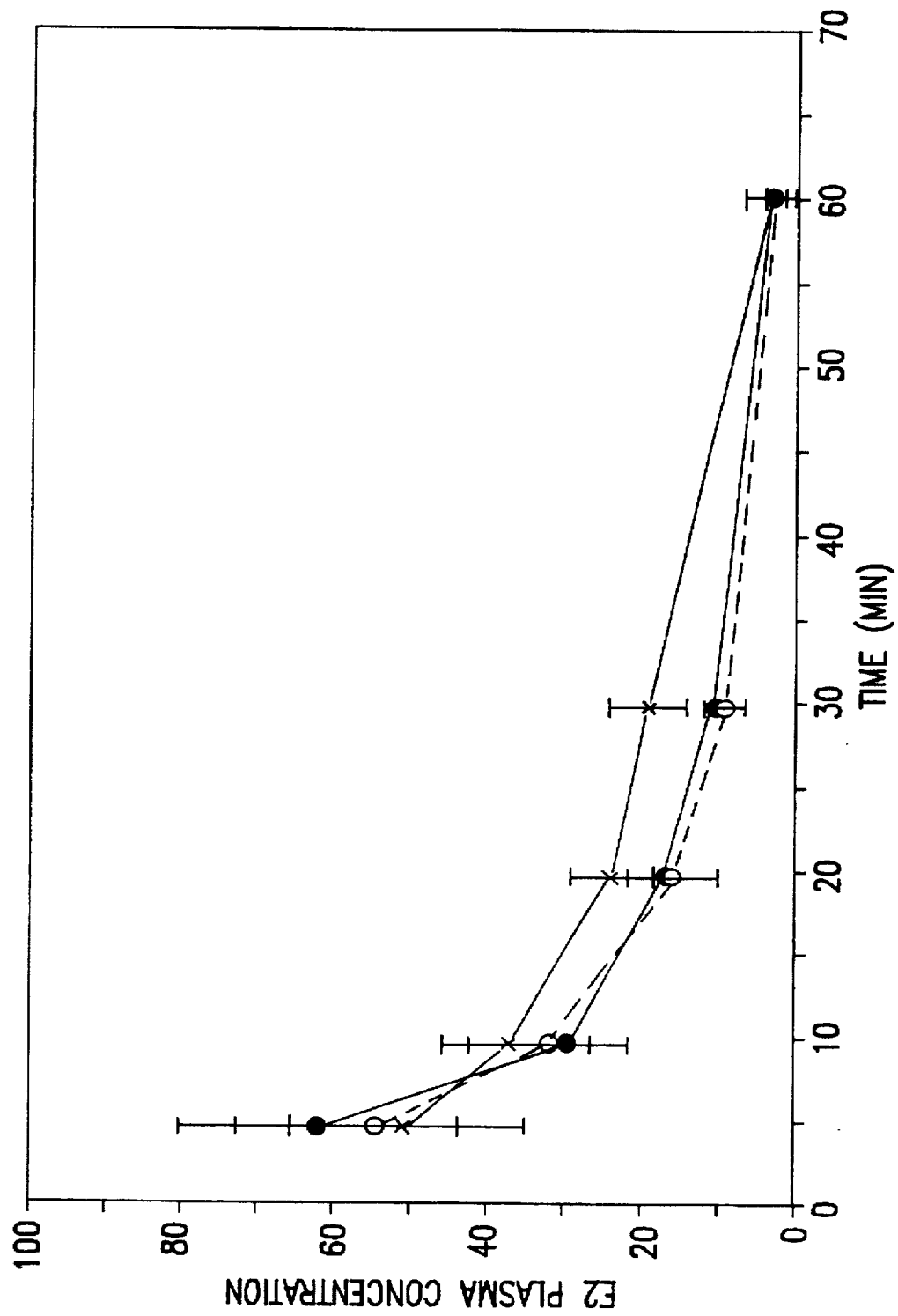
Figure 12:
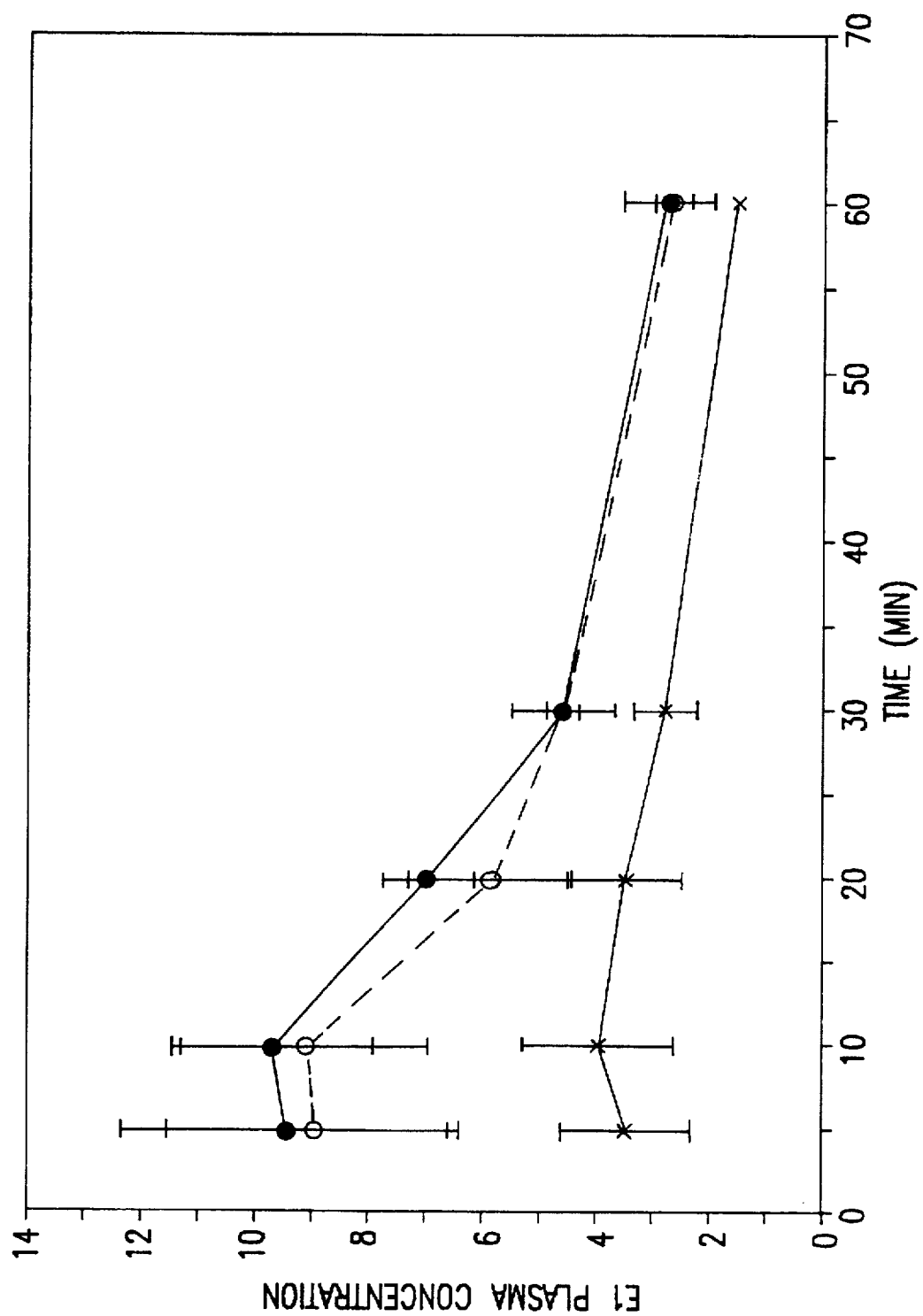
Figure 13:
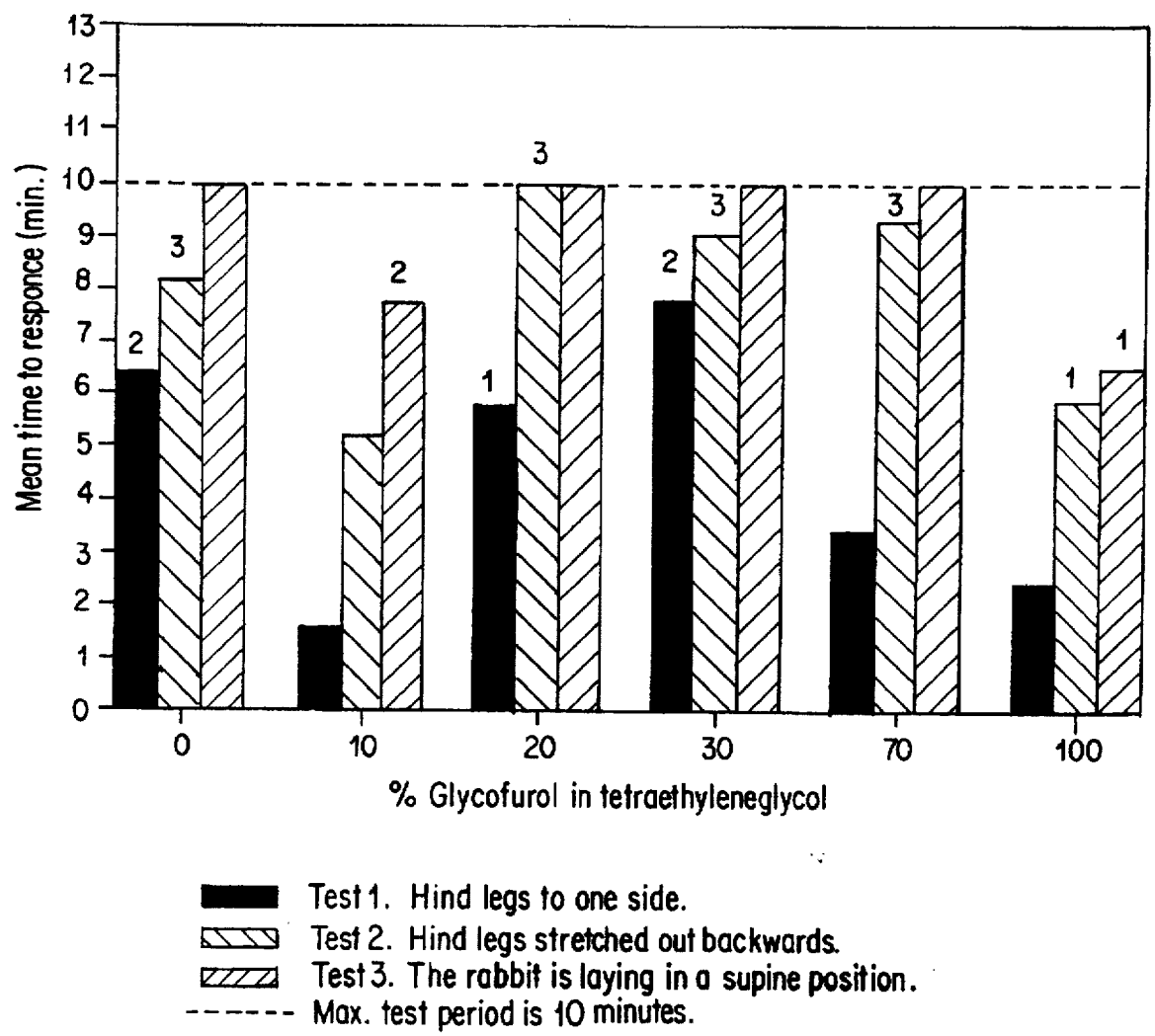
Figure 14:
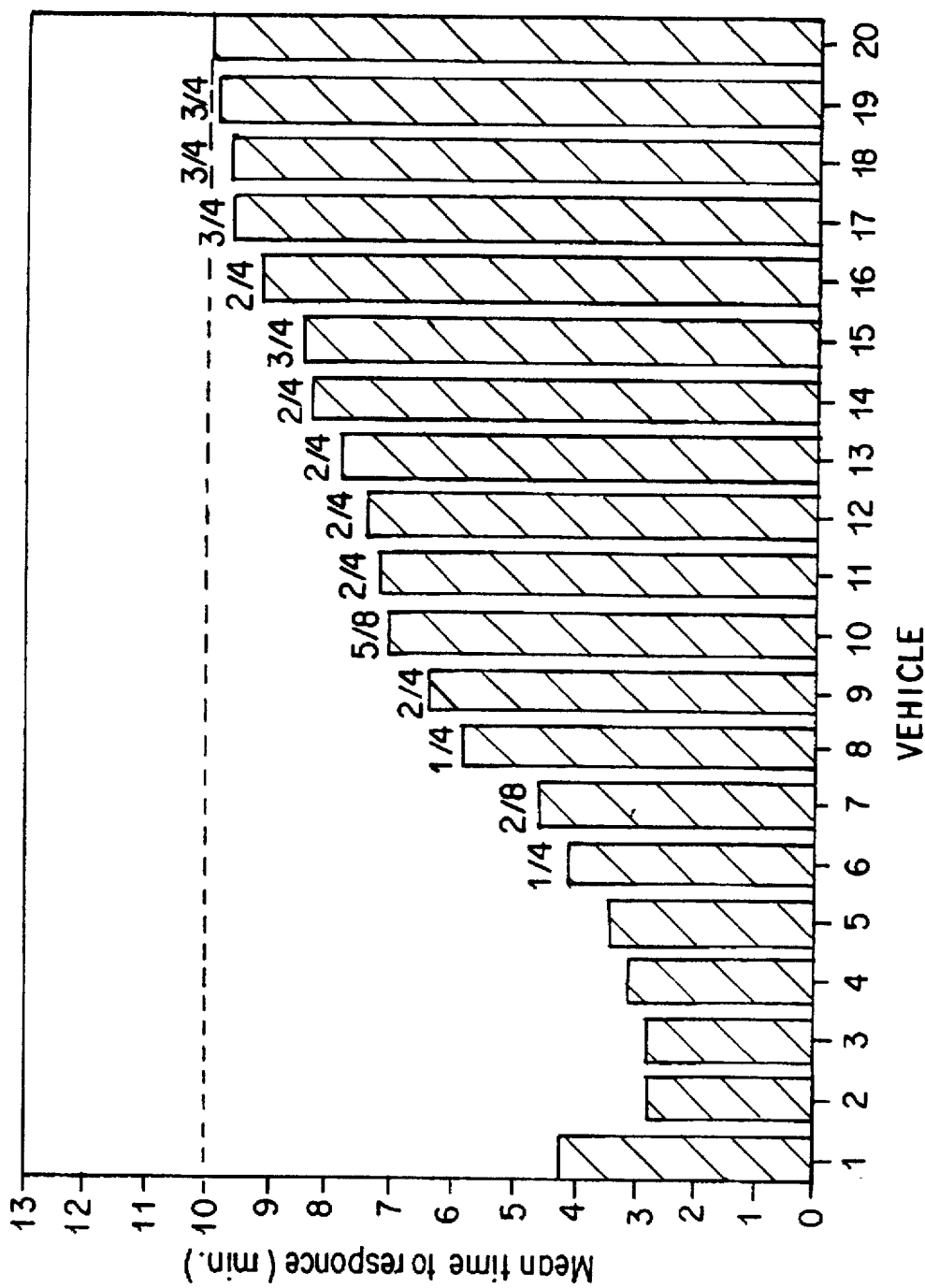
Figure 15:
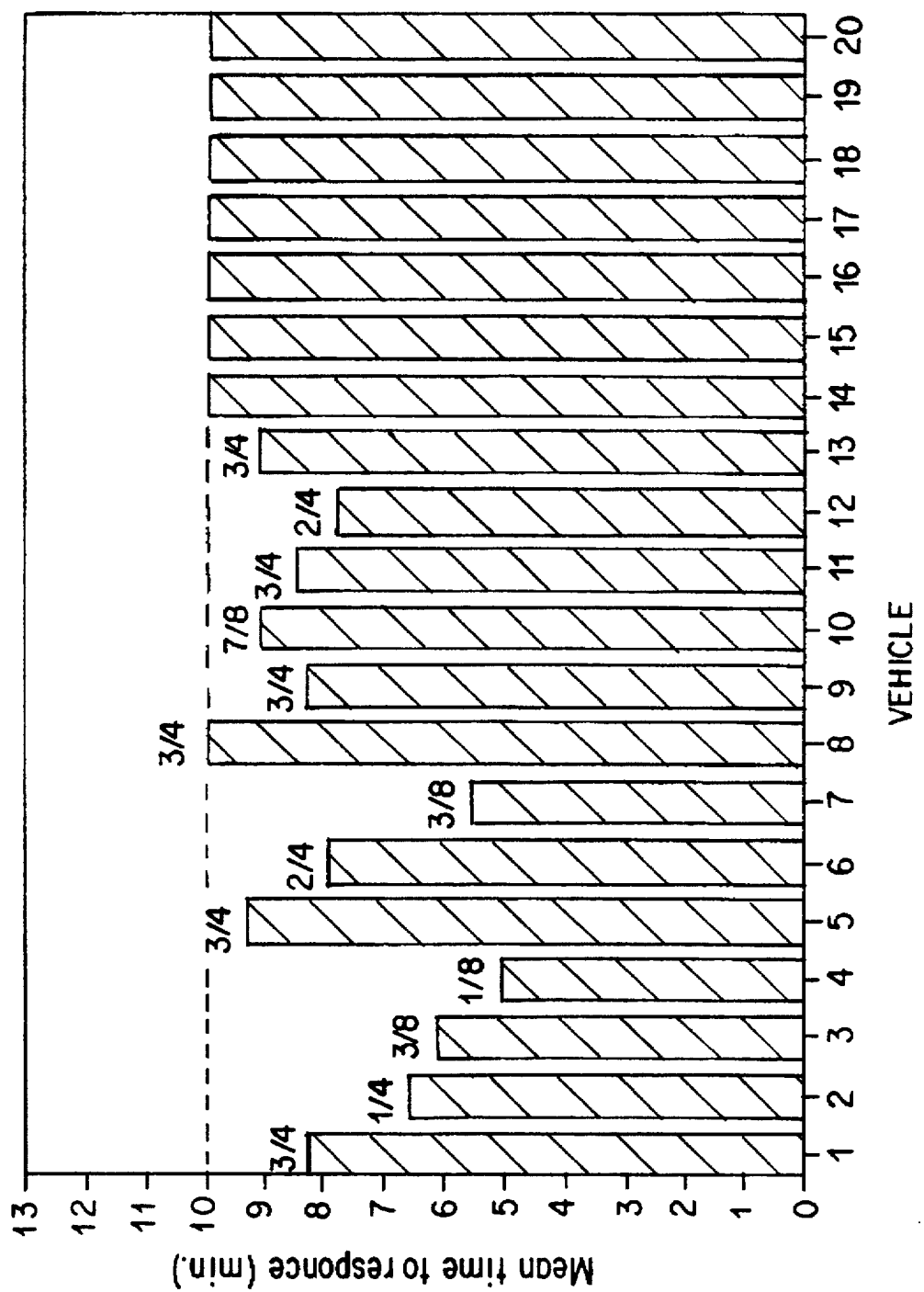

The invention is further illustrated with reference to the accompanying drawings in which FIG. 1 shows a graphical representation of the mean plasma concentration of Clonazepam after intravenous administration and intranasal administration of a preparation in accordance with the invention, FIG. 2 shows a block diagram of the mean time to response as a function of the contents of glycofurol in a prepartion according to the invention, FIG. 3 shows a graphical representation of the blood glucose level after administration of insulin in accordance with the invention, FIG. 4 shows a graphical representation of the blood glucose level after administration of glucagon in accordance with the invention, FIG. 5 shows a graphical representation of the concentration of Clonazepam in plasma after administration of a preparation comprising various ethylene glycol constituents, FIG. 6 shows a graphical representation showing the mean plasma level of diazepam after administration of preparations comprising glyycofuryol and various co-solvents, FIG. 7 shows a graphical representation of the effect of various contents of glycyofurol in preparations according to the invention, FIG. 8 shows a graphical representation comparing the plasma level of flunitrazepam after i.v. administration and intranasal administration according to the invention, FIG. 9 shows a graphical representation comparing the plasma level of clonazepam after i.v. administration and intranasal administration according to the invention, FIG. 10 shows a diagram showing the stability of clonazepam in various vehicles, FIG. 11 shows a graphical representation comparing the plasma concentrations of estrogen after i.v. administration and intranasal administration according to the invention, FIG. 12 shows a graphical representation comparing the plasma concentrations of estrone after i.v. administration and intranasal administration of estrogen according to the invention, FIG. 13 shows a block diagram of the influence of glycofurol on the mean time to response after intranasal application according to the invention, FIG. 14 shows a summary of the mean results for test 1 from Table 1–5, FIG. 15 shows a summary of the mean results for test 2 from Table 1–5, and FIG. 16 shows a summary of the mean results for test 2 from Table 1–5.

The invention is explained more in detail with reference to the Examples which are to be considered only as illustrating the invention and not to be construed so as to limit the scope of the invention as set forth in the appended claims.

EXAMPLE 1

Toxicity and Acceptability study of the vehicles according to the invention

In a toxicological evaluation of the vehicle the local as well as the systemic effect after absorption should be considered. GF and PEG 400 is used as excipient in injection formulations, where the administered amount is greater than 300 μl per dose, which exceeds the amount administered intranasally using the compositions according to the invention.

Local toxicity related results for nEG and GF after intranasal administration are not available from the literature. Therefore, tests were conducted assessing the local toxicity of 30–100 μl to rabbit nasal mucosa. In these tests benzodiazepines were also dissolved in various solvent systems according to the invention and 30 μl of the composition was applied daily for 14 days to the nasal mucosa of rabbits. The effect of the thus administered compositions was then assessed in five experiments including a control carried out as stated in Table 2:

TABLE 2

Assessment of local toxicity of benzodiazepine compositions according to the invention.

| Animal No/Sex | Group | Test Material | Session/Day |
|---|---|---|---|
| 1 m | | | |
| 2 | | | |
| 3 | 1 | 30 μl Saline | 1 |
| 4 f | Control | | |
| 5 | | | |
| 6 | | | |
| 7 m | | | |
| 8 | | | |
| 9 | 2 | 30 μl D in PEG | 1 |
| 10 f | | | |
| 11 | | | |
| 12 | | | |
| 13 m | | | |
| 14 | | | |
| 15 | 3 | 30 μl L in PEG | 1 |
| 16 f | | | |
| 17 | | | |
| 18 | | | |
| 19 m | | | |
| 20 | | | |
| 21 | 4 | 30 μl F in PEG | 1 |
| 22 f | | | |
| 23 | | | |
| 24 | | | |
| 25 m | | | |
| 26 | | | |
| 27 | 5 | 30 μl F in PEG + GF | 1 |
| 28 f | | | |
| 29 | | | |
| 30 | | | |

Abbreviations:
D = Diazepam 3%; L = Lorazepam 5%; F = Flunitrazepam 1%; PEG = Polyethylene glycol 200; GF = Glycofurol 75; PEG + GF = 70% PEG + 30% GF.

Assessment of local toxicity of vehicles of compositions according to the invention.

| Animal No/Sex | Group | Test Material | Session/Day |
|---|---|---|---|
| 1 m | | | |
| 2 | | | |
| 3 | A | 100 μl Saline | 3 |
| 4 f | Control | | |
| 5 | | | |
| 6 | | | |
| 7 m | B | 30 μl PEG | 1 |
| 8 | C | 100 μl PEG | 1 |
| 9 | D | 100 μl PEG | 3 |
| 10 f | E | 30 μl PEG + GF | 1 |
| 11 | F | 100 μl PEG + GF | 1 |
| 12 | G | 100 μl PEG + GF | 3 |
| 13 m | B | 30 μl PEG | 1 |
| 14 | C | 100 μl PEG | 1 |
| 15 | D | 100 μl PEG | 3 |
| 16 f | E | 30 μl PEG + GF | 1 |
| 17 | F | 100 μl PEG + GF | 1 |
| 18 | G | 100 μl PEG + GF | 3 |
| 19 m | E | 30 μl PEG + GF | 1 |
| 20 | F | 100 μl PEG + GF | 1 |
| 21 | G | 100 μl PEG + GF | 3 |
| 22 f | B | 30 μl PEG | 1 |
| 23 | C | 100 μl PEG | 1 |
| 24 | D | 100 μl PEG | 3 |
| 25 m | E | 30 μl PEG + GF | 1 |
| 26 | F | 100 μl PEG + GF | 1 |
| 27 | G | 100 μl PEG + GF | 3 |
| 28 f | B | 30 μl PEG | 1 |
| 29 | C | 100 μl PEG | 1 |
| 30 | D | 100 μl PEG | 3 |

Abbreviations:
A = Control; PEG = Polyethylene glycol 200; GF = Glycofurol 75; PEG + GF = 70% PEG + 30% GF.

The nasal cavity was examined histologically and only mild inflammatory changes were found after the administration of the compositions. No clear dose related response was found with increasing doses and no difference between 100% EG-200 and 70% PEG-200+30% GF was found. It was concluded that he vehicles according to the invention will only incur mild reversible toxicological effects.

The tolerance to two test vehicles containing teytraethylene glycol (4EGf) and optionally 5% glycofurol (GF) was studied after intranasal application in nine healthy volunteers, and compared, after a double blind three way cross-over design, with the vehicle of a marketed product, Locilan® (Astra-Syntex Scandinavia AB, Södertälje, Sweden). As control saline (0.9% sodium chloride) was used.

Saline and the vehicle of the marketed product were very well tolerated. The two vehicles containing tetraethylene glycol caused burning sensation or stinging and runny nose of moderate severity immediately after application. The symptoms were short lasting, being over or only of mild severity 10 min. after application. No clinical symptoms could be observed by nasoscopy 30 minutes after the application.

When questioned all subjects stated, that the 4EGf-containing vehicles optionally comprising 5% GF were acceptable for administration of essential biologically active substances to be used occasionally, and that they would prefer intranasal application in one of these vehicles to intravenous administration.

The experimental details and results are given below.
Acceptability study of the vehicles according to the invention in human subject
Subjects Nine healthy volunteers were enrolled in the trial. All subjects were healthy without any cardiac, hepatic or nephrological diseases.

None of the subjects were suffering from any pulmonary or respiratory diseases or had had a cold within the last 2 weeks. Vital signs (blood pressure and pulse) were within normal range for all subjects. Standard tests for biochemistry and haematology were carried out within two weeks prior to the study. In all but two subjects , all clinical chemical data were within normal range. In subject nos. 4 and 5 alanine aminotransferase (SPGT) was above upper normal limit, but this was considered without clinical significance.
Study procedure The study was a double blind test of three test vehicles and a control (saline) and consisted of three identical sessions, with 24 hours between each session.

During each session a control vehicle was administered into the right nostril 5 minutes prior to application of a test vehicle into the left nostril. The subjects were asked to record in a questionnaire any pain or irritation that was observed 0–1 min. after application, and 10 and 30 minutes after application of the test vehicle. If any symptoms were noted, the subject were to record the severity and to characterize the symptom(s).

Prior to application of vehicles and 30 minutes after application of the test vehicle the mucous membrane in both nostrils were inspected by the experimentor by nasoscopy.
Vehicles Four vehicles were tested, one being saline and used as a negative control. The other three vehicles were two test vehicles according to the invention (Vehicle A and B) and a "positive control", which is the vehicle of a very well tolerated marketed product, Locilan® (Nielsen et al., 1989).
Devices A Pfeiffer pump (model 6917.5902/3790.0129) unit delivering 50 μl when activated was used for application.
Dosage The vehicles were applied after placing the spray unit of the Pfeiffer pump in the left (or right) nostril and activating the pump twice, the total dose being 100 μl.
Clinical inspection The clinical inspection of the tissue in the nose did not disclose any clinical significant effect of the applicated vehicles. In three of the subjects a mild degree of local irritation was noted 30 minutes after application of the vehicles; the vehicles applied being saline in one subject and test vehicle B in the other two subjects.

Tolerance as reported by the subjects (Table 3–5)

The severity of irritation (symptoms) in the nose 0–1 min., 10 min. and 30 min. after application of test vehicles is summarized in table 3, 4, and 5, respectively.

The subjects concluded that the tetraethyleneglycol vehicles optionally comprising glycofurol were less well tolerated than saline of the vehicle in Locilan®. However, the symptoms caused by the 4EGf-containing vehicles were relatively short lasting and considered acceptable, if the biologically active substances were essential for the individual's health.

TABLE 3

Tolerance 0–1 min. after application as reported in questionnaires by the subjects: No. of subjects having symptoms and severity thereof.

| Severity of irritation | Control (right nostril) | Vehicle A | B | C |
|---|---|---|---|---|
| No irritation | 25 | 1 | 0 | 6 |
| Mild-acceptable | 2 | 5 | 3 | 3 |
| Moderate severe | 0 | 3 | 6 | 0 |
| Unacceptable | 0 | 0 | 0 | 0 |

A = 4EGf - vehicle
B = 5% GF in 4EGf
C = Locilan ® vehicle
Control = (right nostril) saline.

TABLE 4

Tolerance 10 min. after application as reported in questionnaires by the subjects: No. of subjects having symptoms and severity thereof.

| Severity of irritation | Control (right nostril) | Vehicle A | B | C |
|---|---|---|---|---|
| No irritation | 27 | 5 | 5 | 7 |
| Mild/acceptable | 0 | 4 | 4 | 2 |
| Moderate severe | 0 | 0 | 0 | 0 |
| Unacceptable | 0 | 0 | 0 | 0 |

A = 4EGf - vehicle
B = 5% GF in 4EGf
C = Locilan ® vehicle
Control = (right nostril) saline.

TABLE 5

Tolerance 30 min. after application as reported in questionnaires by the subjects: No. of subjects having symptoms and severity thereof

| Severity of irritation | Control (right nostril) | Vehicle A | B | C |
|---|---|---|---|---|
| No irritation | 27 | 8 | 7 | 8 |
| Mild/acceptable | 0 | 1 | 2 | 1 |

TABLE 5-continued

Tolerance 30 min. after application as reported in questionnaires by the subjects: No. of subjects having symptoms and severity thereof

| Severity of irritation | Control (right nostril) | Vehicle A | B | C |
|---|---|---|---|---|
| Moderate severe | 0 | 0 | 0 | 0 |
| Unacceptable | 0 | 0 | 0 | 0 |

A = 4EGf - vehicle
B = 5% GF in 4EGf
C = Locilan ® vehicle
Control = (right nostril) saline.

Vehicle A:
Egf-vehicle

| Tetraethylene glycol puriss p.a. | 25 ml |
|---|---|
| Concentrated nitric acid p.a. | 1 drop |
| Tetraethylene glycol puriss p.a. | 25 ml |
| Solution I (app. 30 drops) | ad pH 3.8 |

The mixture I is used to adjust the pH of II employing a pH-electrode for viscous liquids (Radiometer GK 2711). 2–10 ml of II (vehicle A) is dispensed in a Pfeiffer multidispenser (Pfeiffer Zerstäuber, 6917.5902/3790.0129).

Vehicle B:
5% GF in 4EGf-vehicle

| Tetraethylene glycol puriss p.a. | 25 ml |
|---|---|
| Concentrated nitric acid p.a. | 1 drop |
| Tetraethylene glycol puriss p.a. | 25 ml |
| Solution I (app. 30 drops) | ad pH 3.8 |
| Solution II | 23.75 ml |
| Glycofurol 75 purises | 1.25 ml |

The mixture I is used to adjust the pH of II using a pH-electrode for viscous liquids (Radiometer GK 2711). Then the mixture III (vehicle B) is prepared. 2–10 ml of the vehicle is dispensed in a Pfeiffer multidispenser (Pfeiffer Zerstäuber; 6917.5902/3790.0129).

Vehicle C:
Lokilan ®-vehicle

| Propylene glycol, Ph.Eur. III | 2 g |
|---|---|
| Polyethylene glycol 400, Ph.Nord. 63 II | 20 g |
| Tween 20, Ph.Eur. III | 2.5 g |
| Benzalconium chloride, DLS 86 | 70 mg |
| Disodium-EDTA, Ph.Eur. 2nd Ed. 1983 | 10 mg |
| Butylated hydroxytoluene, Ph.Nord. 63 II, Add. | 10 mg |
| Citric acid, Ph.Eur. III, Suppl. 77 | 5 mg |
| Sodium citrate, 2H$_2$O, Ph.Eur. III | 7.65 mg |
| Sorbitol DAK 63 | 2.86 g |
| Purified water, Ph.Eur. 2nd Ed. 1981 | ad 100 g |

EXAMPLE 2

10 mg clonazepam was dissolved in 2 ml of vehicle B (example 1) using ultrasound to obtain a clonazepam concentration of 5 mg/ml. 50 µl of his preparation was administered into each nasal cavity of male New Zealand White rabbits, held in a supine position during and 1 minute after the application. An Eppendorph pipette was used for the application. Blood samples were obtained from the marginal ear vein at 0, 2, 5, 10, 15, 30 and 60 minutes and the clonazepam concentration was determined by HPLC.

FIG. 1 shows the mean plasma clonazepam concentration obtained after the administration. The figure also shows the plasma concentration after i.v. injection into the marginal ear vein of the same dose (0.5 mg) of clonazepam as Rivotril®, injected over ½ minute. The figure shows that the plasma concentration after intranasal application is about the same or even higher, at about 2 minutes, than for an i.v. injection.

EXAMPLE 3

Pharmacodynamic response, enhanced by GF

The pharmacodynamic response was tested in New Zealand White rabbits after application of 50 µl of 2.5 mg clonazepam/ml vehicle into each nostril while they were in sitting position. The vehicle consisted of 0, 10, 20, 30, 70 and 100% glycofurolum 75 (Roche, Lot no. 706127) added to tetraethylene glycol (Merck, Art. 808619). Clonazepam was dissolved by ultrasonification.

FIG. 2 shows the mean time to response (rabbit can stay in a lying position with its hind legs stretched to one side). Number on the top of bars denote the amount of responders out of four tested. Non responders within 10 minutes are calculated as 10 minutes in the mean value. For intranasal administration of clonazapam about 10% GF in 4EGm has an optimal response, whereas about 30% GF has a minimal response. The same pattern is observed for 30% GF in 4EGf.

EXAMPLE 4

0.33 mg zinc-free (monomeric) human insulin in 50 µl 12.5 mM phosphate buffer (pH 7.4) containing 5% glycofurol 75 was applied into one nostril of 5 sitting New Zealand White rabbits, weighing about 3 kg. Blood samples of 50 µl were withdrawn from the marginal ear vein after 0, 15, 30, 60 and 120 minutes, and blood glucose level was determined.

FIG. 3 shows the mean blood glucose level as percentage of initial for the formulation and for 0.9% sodium chloride control. 100 µl of the same formulation, but without insulin, was administered to the nasal cavity of healthy volunteers.

This formulation could not be distinguished from 0.9% sodium chloride with respect to local irritation.

EXAMPLE 5

4 mg human glucagon in 100 µl phosphate buffer (pH 4) containing 5% GF was applied into both nostrils (50 µl into each) of 5 sitting hypoglycaemic New Zealand White rabbits, weighing about 3 kg. The formulation was prepared by dissolving glucagon in a 7 mM phosphate buffer (pH 2.5), adjusting the pH to 4.0 with 0.1N sodium hydroxide and finally 5% glycofurolum 75 was added. The rabbits were made hypoglycaemic by subcutaneous injection of 83 g insulin one hour prior to the experiment. Blood samples were continuously withdrawn from the marginal ear vein for blood glucose determination.

FIG. 4 shows the mean blood glucose level as percentage of initial after the intranasal application of glucagon.

EXAMPLE 6

Control of peak value, Pharmacokinetics 10 mg clonazepam was dissolved in 2 ml of following vehicles: (1) 4EGf, (2) PEG-200 and (3) 4EGm (from MERCK-Schuchardt) using ultrasound. 50 µl of this preparation was administered into each nasal cavity of sitting New Zealand White rabbits by means of an Eppendorph pipette. Blood samples were obtained from the marginal ear vein at following time intervals: 0, 2, 5, 10, 15, 30 and 60 minutes and the clonazepam concentration was determined by HPLC.

FIG. 5 shows the mean plasma clonazepam concentration obtained after the intranasal administration. At about 2 minutes the plasma concentration is higher for the 4EGf than for the PEG-200 and 4EGm formulations.

EXAMPLE 7

Control of peak value, Pharmacokinetics 3 mg diazepam in 100 µl vehicle was prepared and applied to rabbits in a manner analogous to that described in example 6. The following vehicles were used: (1) Glycofurolum 75 (GF); (2) Miglyol 840+GF (7+3) and (3) Vegetable oil+GF (7+3). Blood samples were obtained from the marginal ear vein at following time intervals: 0, 5, 10, 15, 30 and 60 minutes and the diazepam concentration was determined by HPLC.

FIG. 6 shows the mean plasma diazepam concentrations obtained after the intranasal administration. An initial peak plasma concentration can be controlled dependent on the GF/oil vehicle used. The plasma concentration for the GF formulation at 5 minutes is about 55% of an intravenous injection of 3 mg diazepam as Stesolid® (Dumex A/S, Denmark).

EXAMPLE 8

Control of peak value, the role of GF as an enhancer 0.5 mg clonazepam in 100 µl vehicle was prepared and applied to rabbits in a manner analogous to that described in example 6. The following vehicles were used: (1) tetraethylene, glycol (Merck) (4EGm); (2) 2% glycofurol 75 (GF) in 4EGm; (3) 5% GF in 4EGm: (4) 10% GF in 4EGm; (5) 30% GF in 4EGm and (6) GF. Blood samples were obtained from the marginal ear vein at following time intervals: 0, 5, 10, 15, 30 and 60 minutes and the clonazepam concentration was determined by HPLC.

FIG. 7 shows the mean plasma clonazepam concentrations obtained after the intranasal administration. An initial peak plasma concentration can be controlled dependent on the GF/4EGm ratio in the formulation.

EXAMPLE 9

0.5 mg flunitrazepam in 100 µl vehicle was prepared and applied to rabbits in a manner analogous to that described in example 6. The following vehicle was used: Polyethylene glycol 200 (Merck Art. 807483). Blood samples were obtained from the marginal ear vein at following time intervals: 0, 5, 10, 15, 30 and 60 minutes and the flunitrazepam concentration was determined by HPLC.

FIG. 8 shows the mean plasma flunitrazepam concentrations obtained after intranasal and intravenous (Rohypnol®, Roche) administration of 0.5 mg flunitrazepam.

EXAMPLE 10

4 mg midazolam in 100 µl vehicle was prepared and applied to rabbits in a manner analogous to that described in example 6. The following vehicle was used: Polyethylene glycol 200 (Merck, Art. 807483). Blood samples were obtained from the marginal ear vein at following time intervals: 0, 5, 10, 15, 30 and 60 minutes and the midazolam concentration was determined by HPLC.

FIG. 9 shows the mean plasma midazoylam concentrations obtained after intranasal and intravenous (Dormicum®, Roche) administration of 4 mg midazolam.

EXAMPLE 11

Stability studies

In an attempt to optimize the stability of clonazepam in the vehicles according to the invention, an accelerated study was performed. The stability of clonazepam was studied over one month period at 25° and 60° C., where recovery of about 90% or more at 60° C. was considered as very satisfying.

Following formulations were prepared, containing 5 mg/ml clonazepam, except for formulation (1) containing 20 mg/ml; (1) and (2) in 4EGf; (3) as (2) adjusted to pH 3.5 with phosphoric acid; (4) as (2) adjusted to pH 3.5 with citric acid; (5) as (2) added ethanol 9%; (6) as (2) adjusted to pH 3.5 with nitric acid (less than 0.01%); (7) as (2) added water 1%; (8) propylene glycol (PG); (9) as (8) adjusted to pH 3.8 with 0.04% acetic acid; (10) as (2) added acetic acid 0.4%; (11) 4EGf+5% GF added acetic acid 0.4% (pH about 6); (12) as (11) added nitric acid to pH 2. (13) as (11) added benzyl alcohol 3%; (14) as (10) added ethanol 16% and benzyl alcohol 3%; (15) 4EGf+5% GF adjusted to pH 3.5 with nitric acid (less than 0.01%); (16) as (15) added sodium nitrate 0.04%; (17) as (15) added ethanol 5%; (18) 4EGf+ 5% GF adjusted to pH 4.2 citric acid (0.1%); (19) as (15) added benzyl alcohol 2%; (20) 4EGf+5% GF added sodium nitrate 0.04%.

After 2 and 4 weeks 100 µl samples were withdrawn from the containers and analyzed quantitatively by means of HPLC. Sample concentration (and recovery) was calculated on the basis of the peak height relative to an external clonazepam standard.

As seen in table 7, only nitric acid, nitrate, ethanol and benzyl alcohol increases the stability. The content of water in 4EGf, GF and PG was about 0.05%. Amazingly the stability in e.g. 4EGf was not decreased by addition of 1% water. Further, the stability at 25° C. was the same for formulations stored in ampoules (under $N_2$) and in 10 ml Pfeiffer pump (model 6917.5902/3790.0129).

FIG. 10 is a schematic diagram over the stability of clonazepam in the various vehicles,

TABLE 7

STABILITY OF CLONAZEPAM AT 25° C. AND 60° C. IN VARIOUS VEHICLES.
% RECOVERY AFTER 2 AND 4 WEEKS

| No. | Form. | 2 WEEKS Amp. (-air) | | Spraybott. | 4 WEEKS Amp. (-air) | | Spraybott. |
|---|---|---|---|---|---|---|---|
| | | 25° C. | 60° C. | 25° C. | 25° C. | 60° C. | 25° C. |
| 1. | 4 EGf 20 mg/ml | 98 | 91 | 100 | 82 | 73 | 87 |
| 2. | 4 EGf 5 mg/ml | 98 | 82 | 96 | 83 | 61 | 84 |
| 3. | 4 EGf pH 3.5 (Phosphate) | 98 | 79 | 100 | 84 | 62 | 85 |
| 4. | 4 EGf pH 3.5 (Oxalic acid) | 95 | 43 | 95 | 81 | 18 | 82 |
| 5. | 4 EGf Ethanol 9% | 100 | 90 | 99 | 85 | 71 | 90 |
| 6. | 4 EGf pH 3.8 (Nitric acid) | 98 | 88 | 97 | 95 | 87 | 95 |
| 7. | 4 EGf Water 1% | 94 | 83 | 94 | 89 | 71 | 94 |
| 8. | PG | 96 | 69 | 99 | 96 | 56 | 92 |
| 9. | PG pH 3.8 (Acetic acid) | 100 | 99 | 103 | 93 | 95 | 97 |
| 10. | 4 EGf + 0.4% (Acetic acid) | 102 | 84 | 102 | 99 | 67 | 102 |
| 11. | 4 EGf + 5% GF Acetic acid 0.4% | 101 | 80 | 100 | 98 | 63 | 99 |
| 12. | = No. 11 pH 2 (Nitric acid) | 98 | 86 | no data | 97 | 81 | no data |
| 13. | = No. 11 + Benzyl-OH 3% | 103 | 85 | 102 | 99 | 76 | 96 |
| 14. | = No. 10 + Ethanol 16% Benzyl-OH 3% | 103 | 92 | no data | 100 | 80 | no data |
| 15. | 4 EGf + 5% GF pH 3.8 (Nitric acid) | 99 | 94 | 96 | 96 | 96 | 98 |
| 16. | = No. 15 + Nitrate 0.04% | 102 | 95 | 100 | 96 | 93 | 98 |
| 17. | = No. 15 + Ethanol 5% | 96 | 98 | 99 | 98 | 87 | 98 |
| 18. | 4 EGf + 5% GF pH 4.2 (Citric acid) | 95 | 85 | 94 | 93 | 67 | 98 |
| 19. | = No. 15 + Benzyl-OH 2% | 101 | 96 | 97 | 98 | 93 | 99 |
| 20. | 4 EGf + 5% GF + Nitrate 0.04% | 93 | 75 | 99 | 99 | 78 | 95 |

Concentration:
Formulation No. 1 = ca. 20 mg C/ml
Formulation No. 2–10 = ca. 5 mg C/ml
Formulation No. 11–20 = ca. 5 mg C/ml

EXAMPLE 12
Acute toxixological study

This study was conducted in order to observe acute changes in the rabbit nasal cavity after a single dose of vehicle in each nasal cavity. Vehicles tested were glycofurol 75, tetraethylene glycol (Fluka) and propylene glycol (DLS-quality, Mecobenzon, Denmark).

16 rabbits were randomized into 4 groups of 4 rabbits each. 3 groups received a single intranasal application of one of the test vehicles, 50 µl into each nasal cavity. Each rabbit received only one test compound. One group served as a control receiving the same volume of isotonic sodium chloride saline. 10 minutes after application the rabbits were sacrificed and bled. The right nasal cavity was then opened and evaluated macroscopically. The evaluator was blind as to the dosing scheme. The left nasal cavity was dissected and fixed in neutral buffered formalin for histological evaluation.

Macroscopic and microscopic observations in each rabbit 1–16 are given in table 8 and summarized in table 9 with respect to the four vehicles. Amazingly no macroscopic or microscopic difference was seen between isoytonic saline and the 3 vehicles tested.

TABLE 8

OBSERVATIONS OF RABBIT NASAL CAVITIES
10 MINUTES AFTER INTRANASAL APPLICATION OF VEHICLE
N.A. = No Abnormalities    L = Level

| Macroscopic Observations (Right Cavity) | Microscopic Observations (Left Cavity) |
|---|---|
| 1. N.A. | L 1 Congestion |
| | L 2 Focal lymphoid aggregates |
| | L 3 N.A. |
| | L 4 N.A. |
| 2. Slightly hyperaemic | L 1 Congestion |
| | L 2 Focal haemorrhage; congestion |
| | L 3 Focal lymphoid aggregates |
| | L 4 N.A. |
| 3. N.A. | L 1 Congestion |
| | L 2 congestion |
| | L 3 Congestion |

TABLE 8-continued

**OBSERVATIONS OF RABBIT NASAL CAVITIES  
10 MINUTES AFTER INTRANASAL APPLICATION OF VEHICLE  
N.A. = No Abnormalities    L = Level**

| Macroscopic Observations (Right Cavity) | Microscopic Observations (Left Cavity) |
|---|---|
| | L 4 Focal submucousal haemorrhage |
| 4. Mucous lining nasal cavity more pale than normal | L 1 Congestion |
| | L 2 Congestion |
| | L 3 Congestion and mucous inspissation |
| | L 4 N.A. |
| 5. 2 mm haemorrhagic focus in anterior | L 1 Congestion |
| | L 2 Congestion, focal haemorrhage and desquamation, edema, small focus of chronic inflammation and focal lymphoid patches |
| | L 3 Lymphoid aggregates |
| | L 4 Area of chronic inflammation |
| 6. 6 × 3 mm area of haemorrhage anterior | L 1 Congestion and a focus of desquamation, minute haemorrh. |
| | L 2 Congestion and area of submuccosal haemorrhage |
| | L 3 N.A. |
| | L 4 Slight congestion |
| 7. N.A. | L 1 Congestion |
| | L 2 Edema, congestion, focal haemor |
| | L 3 Congestion, focal lymphoid aggr |
| | L 4 Diffuse acute and chronic inflammation. Poly & mono nucl. cell. Blood in lymphatics. |
| 8. N.A. | L 1 Congestion |
| | L 2 Congestion with some submucosal haemorrhage, edema |
| | L 3 Congestion with some submucosal haemorrhage, edema |
| | L 4 Congestion with some submucosal haemorrhage, edema. Mucous inspissation submucosal lymphoid aggregatres |
| 9. N.A. | L 1 Congestion and edema |
| | L 2 Congestion and edema |
| | L 3 Congestion and lateral wall mono & polymorphonuclear cell infiltrate with lymphoid aggreg |
| | L 4 Congestion and lateral wall mono & polymorphonuclear cell infiltrate with lymphoid aggreg |
| 10. N.A. | L 1 Congestion |
| | L 2 Congestion with occasional focal lymphoide aggregations |
| | L 3 Edema and congestion |
| | L 4 Focal chronic mononuclear cell infiltrate; dilatation of lymphatics |
| 11. N.A. | L 1 Edema and congestion |
| | L 2 Edema, congestion, focal haemorrhage and submucosal lymphoid aggregates |
| | L 3 Dilatation of venules |
| | L 4 N.A. |
| 12. N.A. | L 1 Congestions; venule dilatation, focal haemorrhage |
| | L 2 Congestion; edema, focal haemorrhage |
| | L 3 Congestion; submucosal lymphoid aggregates |
| | L 4 Congestion; submucosal lymphoid aggregates |
| 13. N.A. | L 1 Congestion |
| | L 2 Congestion, edema, submucosal lymphoid aggregates |
| | L 3 Congestion, edema, submucosal lymphoid aggreates |
| | L 4 Congestion and pronounced lymphoid aggregates |
| 14. 3 mm haemorrhagic focus towards anterior | L 1 N.A. |
| | L 2 Congestion, edema, submucosal lymphoid aggregates |
| | L 3 Congestion, edema, submucosal lymphoid aggregates |
| | L 4 Congestion, edema, submucosal lymphoid aggregates |
| 15. A small abrasion, pinpoint in the anterior area | L 1 Congestion, edema, focal haemorrhage |
| | L 2 Congestion, focal haemorrhage, edema, submucosal lymphoid aggregates |
| | L 3 Congestion, edema, mononuclear cell infiltrate near basal section |
| | L 4 Congestion |
| 16. 4 × 3 mm area of haemorrhage towards anterior | L 1 Congestion; edema |
| | L 2 Congestion, edema, focal haemorrhage and desquamation |
| | L 3 Congestion, edema, submucosal lymphoid aggregates, especially near base |
| | L 4 Edema, submucosal lymphoid aggregates |

TABLE 9

**SUMMARY OF RESULTS OF RABBIT NASAL CAVITIES  
10 MINUTES AFTER INTRANASAL APPLICATION OF  
4 EGf, GF, PG AND 0.9% NaCl  
(ARRANGED BY VEHICLE)  
N.A. = No Abnormalities**

| Vehicle | Animal No. | Macroscopic Results (Right side) | Microscopic Results (Left side) |
|---|---|---|---|
| 0.9% NaCl | 3 | N.A. | Focal haemorrhage |
| | 6 | 6 × 3 mm haemorrhagic focus, ant. section | Focal haemorrhage |
| | 12 | N.A. | Focal haemorrhage |
| | 13 | N.A. | N.A. |
| Glycofurol (GF) | 2 | N.A. | Focal haemorrhage |
| | 8 | N.A. | Focal haemorrhage |
| | 9 | N.A. | N.A. |
| | 16 | 4 × 3 mm haemorrhagic focus, ant. section | Focal haemorrhage |
| Propylene glycol (PG) | 4 | N.A. | N.A. |
| | 5 | 2 mm haemorrhagic focus, ant. section | Focal haemorrhage |
| | 11 | N.A. | Focal haemorrhage |
| | 14 | 2 mm haemorrhagic focus. ant. section | N.A. |
| Tetraethylene glycol (4 EGf) | 1 | N.A. | N.A. |
| | 7 | N.A. | Focal haemorrhage |
| | 10 | N.A. | N.A. |
| | 15 | Pinpoint abrasion, anterior | Focal haemorrhage |

Surprisingly it has been found that the intranasal absorption of e.g. benzodiazepines, such as clonazepam and diazepam, in the vehicles according to the invention is very similar to an intravenous injection (i.v.). From FIG. 1 it appears that the peak clonazepam plasma concentration ($t_{max}$) is reached within less than 2–3 minutes and that the plasma concentration after 2½ minutes ($C_{pL(2½\,min)}$) is about 100% of that obtained by i.v. administration. The choice of the quality of the vehicles, according to the invention, had surprisingly an influence on the rate of absorption. The plasma concentration of clonazepam at 2½ minute is e.g. about 40% higher for 4EGf (quality from Fluka-Chemie AG) than for 4EGm (quality from MERCK-Schuchardt) or PEG 200 (from MERCK-Schuchardt), and $t_{max}$ is about ≤2½, 10 and 15 minutes, respectively (FIG. 5).

The pharmacodynamic response was studied in rabbits. The time to response after intranasal application of 0.25 mg clonazepam pain in 100 µl of vehicle was measured. The mean times are given in FIG. 2 and the experimental details are stated in Example 3. As shown in FIG. 2, a pharmacodynamic response after intranasal administration of clonazepam in the vehicles according to the invention may be obtained in less than 2 minutes after the application.

The compositions of the invention are stable. This has e.g. been demonstrated by measuring benzodiazepine concentration of the compositions according to the invention after a month at 60° C. and at 25° C., respectively (see example 11). A stable solution (recovery about ≥290%) can be obtained using PG after addition of acetic acid (adjusted to pH 3.8–4). The same amount of acetic acid was not able to render the 4EGf solution stable, and the amount of acetic acid needed for the adjusting pH to about 4 was too high. Amazingly adjusting pH using nitric acid resulted in stable solutions of clonazepam in e.g. 4EGf optionally comprising 5% GF (recovery about ≥90%).

Surprisingly, it has also been found that using the vehicles according to the invention together with insulin or glucagon a pronounced biological response is obtained within 15–30 minutes after intranasal application to rabbits (FIGS. 3 and 4, and examples 4 and 5).

EXAMPLE 13

Bioavailability

The bioavailability of estrogen (E2) and estrone (E1), after intranasal (i.n.) application to rabbits (n=3) of a single dose of 50 µg E2, was studied in pilot. Two formulations containing 30% and 100% glycofurol (GF), respectively, were tested i.n. relative to an i.v.-injection of the same dose.

Materials

17-β-estradiol (estrogen=E2) was obtained from Novo Nordisk (Copenhagen, Denmark), propylenglycolum ad infundibilia (PG) from Mecoybenzcn (Copenhagen, Denmark) and glycofurolum 75 (GF) from Hoffman La-Roche (Basel, Switzerland). All other reagents were of reagent or analytical grade.

Drug preparation

The formulations for i.v.-injection and for intranasal application were prepared just before the administration. Formulation 1 for i.v. administration was prepared by dissolving 2.729 mg E2 in 25.0 ml PG and then adding 25.0 ml isotonic saline. Formulation 2 for i.n. application was prepared by dissolving 4.938 mg E2 in 10.0 ml GF. Formulation 3, also for i.n. application, was prepared by dissolving 4.996 mg E2 in 3.00 ml GF and then adding isotonic saline to a total volume of 10.0 ml.

Dosing and study design

Rabbits (n=3) having i.v. administration received 1.0 ml of formulation 1 i.v. (equivalent to 50 µg E2) as an ear-vein infusion during 30 seconds. Rabbits (n=3) having i.n. administration received formulation 2 or 3 i.n. with an Eppendoryph pipette. Each rabbit received 50 µl into each nostril, equivalent to 50 µg E2. The intranasal application occupied about 5 seconds. During and about 1 minute after the intranasal applications, the rabbits were held in a supine position.

Blood samples were collected 0, 5, 10, 20, 30, and 60 minutes after the administration. Plasma was isolated and stored at +20° C. until analysis.

The plasma concentrations of unconjugated E2 and E1 were measured by radioimmunoassay as described by Emmet et al., 1972. After extraction with ether, separation of E1 and E2 was performed on columns of Sephadex LH20. Radioimmunoassay was performed after evaporation of the solvents. The detection limits for E1 and E2 were 40 pmol/l. The intra- and interassay variance for E1 were 7.0% and 9.6%, and for E2 7.4% and 10.5%, respectively.

Dose/weight correction for individual plasma concentrations was calculated relative to the mean of i.v. dose/weigth (22.3 µg/kg). For formulation 1 i.v. the area (AUC) under the E2 plsama concentration-time curves, from 0 min to infinity, a one compartment with 30 seconds infusion was fitted to the data. All other AUC's were calculated by means of the trapezoidal rule.

The plasma concentrations of E2 and E1 after administration of E2 appear from Table 10 and 11 and FIGS. 11 and 12, respectively. FIG. 11 shows the mean ±S.D. estrogen (E2) plasma concentrations after administration of about 50 µg estrogen to rabbits (n=3) as an i.v.-injection (formulation 1) or intranasal administration (2 i.n. and 3 i.n. formulated with glycofurol (GF) 100% and 30%, respectively).

_x_ form. 1 i.v., _●_ form. 2 i.n., and ...o... form. 3 i.n., and FIG. 12 shows the mean±S.D. estrone (E1) plasma concentrations after administration of about 50 µg estrogen to rabbits (n=3) as an i.v.-injection (formulation 1) or intranasal administration (2 i.n. and 3 i.n. formulated with glycofurol (GF) 100% and 30%, respectively).

_x_ form. 1 i.v., _●_ form. 2 i.n., and ...o... form. 3 i.n.

As seen from FIGS. 11 and 12 and Table 12, intranasal application was very similar to i.v administration. The bioavailability appears from Table 12. The bioavailability for E2 was 87 and 80%, and for E2+E1 104 and 95% for formulation 2 i.n. and 3 i.n., respectively. $C_{5min}$ for E2 was 109% and 95%, and fur E2+E1 118% and 105%. $T_{max}$ was shorter than 5 min.

TABLE 10

Individual estrogen (E2) plasma concentrations after administration of about 50 µg estrogen to rabbits (n = 3) as an i.v.-injection (formulation 1) or intranasal administration (2 i.n. and 3 i.n. formulated with glycofurol (GF) 100% and 30%, respectively). n.d. = lower than 0.04 nmol/ml.

| Formula- | Rabbit | E2 plasma concentration (nmol/ml) after min. | | | | | | Dose/ weight |
|---|---|---|---|---|---|---|---|---|
| tion | no. | 0 | 5 | 10 | 20 | 30 | 60 | µg/kg |
| 1. i.v. | 4 | n.d. | 49.0 | 37.0 | 19.0 | 15.0 | 4.90 | 22.2 |
|  | 5 | 0.12 | 65.0 | 45.0 | 29.0 | 18.0 | 7.60 | 21.8 |
|  | 6 | 0.12 | 38.0 | 30.0 | 25.0 | 21.0 | 11.0 | 22.9 |
| 2. i.n. | 1 | 0.19 | 75.0 | 26.0 | 16.0 | 11.0 | 3.70 | 20.1 |
| (100% | 2 | 0.09 | 50.0 | 32.0 | 18.0 | 11.0 | 5.20 | 21.3 |
| GF) | 3 | n.d. | 44.0 | 24.0 | 14.0 | 8.8 | 3.30 | 19.3 |
| 3. i.n. | 7 | 0.10 | 41.0 | 31.0 | 15.0 | 8.7 | 3.90 | 17.5 |
| (30% | 8 | 0.09 | 64.0 | 32.0 | 18.0 | 10.0 | 3.40 | 19.4 |
| GF) | 9 | 0.08 | 31.0 | 17.0 | 8.2 | 5.9 | 1.90 | 18.5 |

TABLE 11

Individual estrone (E1) plasma concentrations after administration of about 50 μg estrogen to rabbits (n = 3) as an i.v.-injection (formulation 1) or intranasal administration (2 i.n. and 3 i.n. formulated with glycofurol (GF) 100% and 30%, respectively). n.d. = lower than 0.04 nmol/ml.

| Formula-tion | Rabbit no. | E1 plasma concentration (nmol/ml) after min. | | | | | | Dose/weight pg/kg |
|---|---|---|---|---|---|---|---|---|
| | | 0 | 5 | 10 | 20 | 30 | 60 | |
| 1. i.v. | 4 | n.d. | 4.30 | 4.30 | 3.10 | 2.70 | 1.60 | 22.2 |
| | 5 | n.d. | 4.00 | 5.10 | 4.60 | 3.30 | 1.50 | 21.8 |
| | 6 | n.d. | 2.20 | 2.60 | 2.80 | 2.30 | 1.50 | 22.9 |
| 2. i.n. | 1 | n.d. | 11.00 | 9.90 | 7.10 | 4.80 | 3.00 | 20.1 |
| (100% | 2 | n.d. | 6.20 | 7.40 | 6.00 | 3.40 | 3.00 | 21.3 |
| GF) | 3 | n.d. | 8.50 | 9.00 | 5.90 | 4.30 | 1.60 | 19.3 |
| 3. i.n. | 7 | n.d. | 8.10 | 8.90 | 5.80 | 3.90 | 2.30 | 17.5 |
| (30% | 8 | n.d. | 5.30 | 6.10 | 5.00 | 3.90 | 2.40 | 19.4 |
| GF) | 9 | n.d. | 8.80 | 7.50 | 3.80 | 3.70 | 1.90 | 18.5 |

TABLE 12

Pharmacokinetic data (dose corrected relative to mean i.v. dose) for estrogen (E2) and estrone (E1) after single administration of about 50 μg estrogen (n = 3) as an i.v. — injection (1 i.v.) or intranasal administration (2 i.n. and 3 i.n.). AUC (nmol ml$^{-1}$ min) is the area under the plasma concentration — time curve from 0 min to infinity. $C_{max}$ (nmol/ml) is the maximal plasma concentration. $t_{max}$ (min) is the time to maximal plasma concentration.

| Parameter | | Observed mean (dose corrected) | | | % Relative to 1 i.v. — mean ± SD | |
|---|---|---|---|---|---|---|
| | | 1 i.v. | 2 i.n. | 3 i.n. | 2 i.n. | 3 i.n. |
| AUC | E$_2$ | 1302 | 1138 | 1038 | 87 ± 11 | 80 ± 30 |
| | E$_1$ | 241 | 471 | 432 | 195 ± 18 | 179 ± 12 |
| | E$_2$ + E$_1$ | 1543 | 1609 | 1470 | 104 ± 13 | 95 ± 25 |
| C$_{max}$ | E$_2$ | 57 | 62 | 54 | 109 ± 29 | 95 ± 35 |
| | E$_1$ | 4 | 10 | 10 | 150 ± 22 | 250 ± 22 |
| | E$_2$ + E$_1$ | 61 | 72 | 64 | 118 ± 28 | 105 ± 33 |
| t$_{max}$ | E$_2$ | 5 | 5 | 5 | 100 ± 0 | 100 ± 0 |
| | E$_1$ | 12 | 8 | 8 | 67 ± 38 | 67 ± 38 |

COMMENTS

The solubility for E2 in GF is found to be about 230 mg/ml. Thus, a clinical dose of 50 μg is soluble in 0.25 μl. Hence, the application of a clinical dose in an extremely small μl-volumen is rendered possible using GF. As the solubility decreases exponentially in combination with water, the dose volume using GF as a vehicle should e.g. be about 5 μl, to avoid unwanted precipitation of E2 in the nasal mucus.

A small dose volume is desirable in order to reduce or eliminate a local irritating effect. Alternatively a non irritating co-solvent, e.g. vegetabile oil, may be added. In this way a desired dose volume or delivery rate may also be obtained. To reduce plasma peak concentration, a limited precipitation of E2 in the mucus may also be desirable.

A anhydrous GF-formulation may be useful in acute hot flushing as well as in chronic dosing.

EXAMPLE 14a

The experiment illustrates, in pilot scale, the influence of the various vehicles on the onset of the pharmacodynamic test in rabbits.

Materials and Methods

Materials for the preparation of the vehicles used are Glycofurolum from Hoffman-La Roche (Lot #706127), tetraethylene glycol from Merck-Schuchardt (Art. 808619), Polysorbatum 20 Ph.Eur. (Tween 20, batch #102382) and Oleum vegetabile tenue DAK 63 (batch #154491) from Mecobenzon, Copenhagen. Ethanol was supplied by Novo Nordisk A/S. 2.5 mg/ml of the active substance, clonazepam (Roche A/S, Hvidovre, Denmark, order #2746A01) was dissolved in the vehicle using a ultrasonic bath. Each rabbit had 50 μl applied in each nostril corresponding to 0.25 mg clonazepam per rabbit with one exception where the rabbit had 0.5 mg (Table 4).

For intravenous application 1.0 ml of Rivotril® from Hoffman-La Roche (comprising 0.5 mg/ml, after dilution, batch #B0447MFD06 87).

Immediately after each application the rabbits were tested as described in the below 3 tests:

1: Hind legs to one side
2: Hind legs stretched out backwards
3: The rabbit is lying in a suppine position

RESULTS AND DISCUSSION

Table 1 indicates tha 10% of GF is at least as efficient as pure GF and apparently better than the remaining mixtures and 4EG.

Table 2 indicates that 5–7.5% of GF is better than 1% and 2.5% of GF. Pure GF is best and corresponds to Table 1 of the experiment. 10% Oleum vegetabile (OV) in GF reduces the time to observed effect considerably.

Table 3 indicates that 5% of GF is better than 10% and 15% and equal to pure GF in the experiments of Tables 1 and 2. Pure 4EG and 9% of Etahnol as well as 5% of Tween 20 is considerably inferior than the above.

Table 4 indicates that application of the same dose in a minor volume (i.e. 25 μl instead of 50 μl in each nostril) does not enhance the effect (as compared with Table 2). 3EG is possibly better than 1, 2.5, and 5t of GF in 4EG but, with respect to toxicity, 4EG will be the direct choice.

Table 5 indicates that intranasal application (of e.g. 10% GF) may act just as quickly as intravenous injection (in 2.8 min (i.n.) and 4.2 min (i.v.), respectively) in spite of the fact that the plasma level is higher after i.v. administration. The reason for this exciting result is not known. One explanation might be that clonazepam is distributed in different manner after i.v. administration, precipitates or is released slowly to the aqueous phase of the blood; however, this is not consistent with the high plasma concentration. Another explanation might be a very rapid rate of passing to the CNS from the nasal cavity.

In short it can be emphasized that GF and 4EG apparently have an optimum mixture of about 5–10%. This is most clear from test 1 in Table 1 and FIG. 1. The tendency is also noticed in Tables 2 and 3 corresponding to the situation that GF in addition to showing good performance in itself, also shows enhancing properties in mixture with 4EG. Generally speaking, test 1 appears to be the most important test as it shows relaxation of muscles already after two minutes.

TABLE 1

THE INFLUENCE OF GLYCOFUROLE (% GF) ON THE TIME TO RESPONSE (minutes)
AFTER INTRANASAL APPLICATION OF 0.25 mg CLONAZEPAM IN TETRAETHYLEN-
GLYCOL (4EG) TO RABBITS (n = 4).
NOTICE: THE TIME (in minutes) IS MEASURED FROM THE START OF EACH APPLICATION
(each application takes about 5-10 seconds).

| TEST: | RABBIT | FORMULATION 1 4EG | FORMULATION 2 10% GF IN 4EG | FORMULATION 3 20% GF IN 4EG | FORMULATION 4 30% GF IN 4EG | FORMULATION 5 70% GF IN 4EG | FORMULATION 6 GF |
|---|---|---|---|---|---|---|---|
| NO. 1 | I | 2.3 | 2.1 | 3.5 | 6.7 | 2.5 | 2.3 |
|  | II | — | 1.2 | 4.8 | — | 1.9 | 1.1 |
|  | III | 3.3 | 1.9 | — | — | 5.1 | 2.6 |
|  | IV | — | 1.3 | 5.0 | 4.3 | 4.0 | 3.5 |
|  | MEAN | >6.4 | 1.6 | >5.8 | >7.8 | 3.4 | 2.4 |
| NO. 2 | I | 2.7 | 3.7 | — | 6.3 | 7.0 | 2.9 |
|  | II | — | 2.0 | — | — | — | 1.5 |
|  | III | — | 10.4 | — | — | — | 9.2 |
|  | IV | — | 4.8 | 10.0 | — | — | — |
|  | MEAN | >8.2 | 5.2 | >10.0 | >9.1 | >9.3 | >5.9 |
| NO. 3 | I | — | — | — | — | — | 6.7 |
|  | II | — | 4.2 | — | — | — | 3.3 |
|  | III | — | — | — | — | — | — |
|  | IV | — | 6.0 | — | — | — | 5.0 |
|  | MEAN | >10.0 | >7.8 | >10.0 | >10.0 | >10.0 | >6.5 |

— NOT RESPONDED WITHIN THE 10 MIN. TEST PERIOD. TO CALCULATE THE MEAN VALUE, ONLY 10 MINUTES ARE INSERTED FOR NON-RESPONDERS.
TEST 1. HIND LEGS TO ONE SIDE
TEST 2. HIND LEGS STRETCHED OUT BACKWARDS
TEST 3. THE RABBIT IS LYING IN A SUPINE POSITION

TABLE 2

THE INFLUENCE OF GLYCOFUROLE (% GF) IN TETRAETHYLENEGLYCOL (4EG) AND
VEGETABILE OIL (OV) IN GF ON THE TIME TO RESPONSE (minutes) AFTER
INTRANASAL APPLICATION OF 0.25 mg CLONAZEPAM TO RABBITS (n = 4).
NOTICE: THE TIME (in minutes) IS MEASURED FROM THE START OF EACH APPLICATION
(each application takes about 5-10 seconds).

| TEST: | RABBIT | FORMULATION 1 1% GF IN 4EG | FORMULATION 2 2.5% GF IN 4EG | FORMULATION 3 5% GF IN 4EG | FORMULATION 4 7.5% GF IN 4EG | FORMULATION 5 GF | FORMULATION 6 10% OV IN GF |
|---|---|---|---|---|---|---|---|
| NO. 1 | I | — | — | 3.1 | 4.0 | 3.2 | 7.0 |
|  | II | 9.7 | — | 2.5 | — | 5.9 | — |
|  | III | — | — | — | — | 3.5 | 2.7 |
|  | IV | — | — | — | — | 2.7 | — |
|  | MEAN | >9.9 | >10.0 | >6.4 | >8.5 | 3.8 | >7.4 |
| NO. 2 | I | — | — | — | — | 3.9 | 7.8 |
|  | II | — | — | 2.57 | — | 6.4 | — |
|  | III | — | — | — | — | 4.5 | 3.3 |
|  | IV | — | — | — | — | 2.9 | — |
|  | MEAN | >10.0 | >10.0 | >8.1 | >10.0 | 4.4 | >7.8 |
| NO. 3 | I | — | — | — | — | 8.0 | — |
|  | II | — | — | — | — | 7.4 | — |
|  | III | — | — | — | — | — | 4.8 |
|  | IV | — | — | — | — | 5.6 | — |
|  | MEAN | >10.0 | >10.0 | >10.0 | >10.0 | >7.8 | >8.7 |

— NOT RESPONDED WITHIN THE 10 MIN. TEST PERIOD. TO CALCULATE THE MEAN VALUE, ONLY 10 MINUTES ARE INSERTED FOR NON-RESPONDERS.
TEST 1. HIND LEGS TO ONE SIDE
TEST 2. HIND LEGS STRETCHED OUT BACKWARDS
TEST 3. THE RABBIT IS LYING IN A SUPINE POSITION

TABLE 3

THE INFLUENCE OF ETHANOL (ETOH), POLYSORBATE 20 (TWEEN 20) AND GLYCOFUROL (% GF) IN TETRAETHYLENEGLYCOL (4EG) ON THE TIME TO RESPONSE (minutes) AFTER INTRANASAL APPLICATION OF 0.25 mg CLONAZEPAN TO RABBITS (n = 4).
NOTICE: THE TIME (in minutes) IS MEASURED FROM THE START OF EACH APPLICATION (each application takes about 5–10 seconds).

| TEST: | RABBIT | FORMULATION 1 4EG | FORMULATION 2 9% ETOH IN 4EG | FORMULATION 3 5% TWEEN 20 IN 4EG | FORMULATION 4 5% GF IN 4EG | FORMULATION 5 10% GF IN 4EG | FORMULATION 6 15% GF IN 4EG |
|---|---|---|---|---|---|---|---|
| NO. 1 | I | — | — | — | 1.8 | 2.9 | 3.7 |
| | II | 1.1 | — | 7.1 | 1.5 | 1.5 | — |
| | III | — | 2.2 | — | 5.7 | 8.6 | — |
| | IV | — | 3.2 | 9.6 | 2.1 | 3.3 | 9.5 |
| | MEAN | >7.8 | >6.4 | >9.2 | 2.8 | 4.1 | >8.3 |
| NO. 2 | I | — | — | — | 2.1 | — | — |
| | II | — | — | — | 3.7 | 2.1 | — |
| | III | — | 3.3 | — | 4.0 | — | — |
| | IV | — | — | — | 3.2 | — | — |
| | MEAN | >10.0 | >8.3 | >10.0 | 3.0 | >8.0 | >10.0 |
| NO. 3 | I | — | — | — | 3.6 | — | — |
| | II | — | — | — | — | — | — |
| | III | — | — | — | 8.0 | — | — |
| | IV | — | — | — | 3.8 | — | — |
| | MEAN | >10.0 | >10.0 | >10.0 | >6.4 | >10.0 | >10.0 |

— NOT RESPONDED WITHIN THE 10 MIN. TEST PERIOD. TO CALUCULATE THE MEAN VALUE, ONLY 10 MINUTES ARE INSERTED FOR NON-RESPONDERS.
TEST 1. HIND LEGS TO ONE SIDE
TEST 2. HIND LEGS STRETCHED OUT BACKWARDS
TEST 3. THE RABBIT IS LYING IN A SUPINE POSITION

TABLE 4

THE INFLUENCE OF FORMULATION ON THE TIME TO RESPONSE (minutes) AFTER INTRANASAL APPLICATION OF 0.25 MG CLONAZEPAN TO RABBITS (n = 4), CONTRARY TO TABLE 1, 2 AND 3, THE APPLIED VOLUME WAS 25 μl TO EACH NOSTRIL INSTEAD OF 50 μl ABBREVIATIONS: GLYCOFUROL (GF), TETRAETHYLENEGLYCOL (4EG) AND TRIETHYLENEGLYCOL (3EG), FORMULATION 1–3 ARE TESTED SAME DAY.
NOTICE: THE TIME (in minutes) IS MEASURED FROM THE START OF EACH APPLICATION. (Each application takes about 5–10 seconds).

| TEST: | RABBIT | FORMULATION 1 1% GF IN 4EG | FORMULATION 2 2.5% GF IN 4EG | FORMULATION 3 5% GF IN 4EG | FORMULATION 4 3EG |
|---|---|---|---|---|---|
| NO. 1 | I | 8.4 | 5.4 | — | 1.4 |
| | II | — | 3.5 | 8.6 | 1.5 |
| | III | — | — | — | — |
| | IV | — | — | — | 3.5 |
| | MEAN | >9.6 | >7.2 | >9.7 | >4.1 |
| NO. 2 | I | — | — | — | 7.9 |
| | II | — | 3.7 | — | 3.9 |
| | III | — | — | — | — |
| | IV | — | — | — | — |
| | MEAN | >10.0 | >8.5 | >10.0 | >8.0 |
| NO. 3 | I | — | — | — | — |
| | II | — | — | — | — |
| | III | — | — | — | — |
| | IV | — | — | — | — |
| | MEAN | >10.0 | >10.0 | >10.0 | >10.0 |

— NOT RESPONDED WITHIN THE 10 MIN. TEST PERIOD. TO CALCULATE THE MEAN VALUE, ONLY 10 MINUTES ARE INSERTED FOR NON-RESPONDERS.
TEST 1. HIND LEGS TO ONE SIDE
TEST 2. HIND LEGS STRETCHED OUT BACKWARDS
TEST 3. THE RABBIT IS LYING IN A SUPINE POSITION

TABLE 5

Time to response (minutes) after the application of 0.5 mg clonazepam intranasally and intravenously to rabbits (n = 4). Abbreviations: Glycofurol (GF) and tetraethylene-glycol (4EG). NOTICE: The time (in minutes) is measured from the start of each application. (Each application takes about 5–10 seconds and 30 seconds for i.n. and i.v. respectively).

| Test: | Rabbit | Intranasal 10% GF in 4EG | Intravenous Rivotril ® |
|---|---|---|---|
| No. 1 | I | 1.6 | 1.2 |
| | II | 5.6 | 9.0 |
| | III | 1.9 | 3.0 |
| | IV | 2.0 | 3.5 |
| | Mean | 2.8 | 4.2 |
| No. 2 | I | 1.9 | 3.0 |
| | II | 7.0 | — |
| | III | 6.0 | — |
| | IV | — | — |
| | Mean | >6.1 | >8.3 |
| No. 3 | I | 2.5 | 3.4 |
| | II | 9.8 | — |
| | III | 9.2 | — |
| | IV | — | — |
| | Mean | >7.9 | >8.4 |

— Not responded within the 10 min. test perid. To calculate the mean value, only 10 minutes are inserted for non-responders.
TEST 1. HIND LEGS TO ONE SIDE
TEST 2. HIND LEGS STRETCHED OUT BACKWARDS
TEST 3. THE RABBIT IS LYING IN A SUPINE POSITION FIG. 13 shows the influence of glycofurol (% GF) on the mean time to response (minutes) after intranasal application of 0.25 mg. clonazepam in tetraethyleneglycol (4EG) to rabbits (n=4) (individual data, see Table 1).

In FIG. 13, the numbers on top of the bars denote the amount of non-responders within 10 minutes test period. Such bars are higher in reality, as only 10 minutes are used for non-responders to calculate the mean.

FIG. 14 shows a summary of the mean results for test 1 (hind legs to one side) from Table 1–5. The numbers on top of the bars denote the amount of non-responders, within the 10 min. test period, relative to the amount tested (such bars are higher in reality, as only 10 min. are used for non-responders to calculate the mean).

| Vehicle no.: | Dose (mg): | Formulation: |
|---|---|---|
| 1 | 0.50 | Rivotril ® IV-injection |
| 2 | 0.50 | 10% GF in 4EG |
| 3 | 0.25 | 10% GF in 4EG |
| 4 | 0.25 | Pure GF |
| 5 | 0.25 | 70% GF in 4EG |
| 6 | 0.25 | Pure 3EG |
| 7 | 0.25 | 5% GF in 4EG |
| 8 | 0.25 | 20% GF in 4EG |
| 9 | 0.25 | 9% EtOH in 4EG |
| 10 | 0.25 | Pure 4EG |
| 11 | 0.25 | 2.5% GF in 4EG[a] |
| 12 | 0.25 | 10% VO in GF |
| 13 | 0.25 | 30% GF in 4EG |
| 14 | 0.25 | 15% GF in 4EG |
| 15 | 0.25 | 7.5% GF in 4EG |
| 16 | 0.25 | 5% Tween in 4EG |
| 17 | 0.25 | 1% GF in 4EG[a] |
| 18 | 0.25 | 5% GF in 4EG[a] |
| 19 | 0.25 | 1% GF in 4EG |
| 20 | 0.25 | 2.5% GF in 4EG |

[a] The drug was applied in 50 µl instead of 100 µl as usual.

FIG. 15 shows a summary of the mean results for test 2 (hind legs stretched out backwards) from Table 1–5. The numbers on top of the bars denote the amount of non-responders, within the 10 min. test period, relative to the amount tested (such bars are higher in reality, as only 10 min. are used for non-responders to calculate the mean).

| Vehicle no.: | Dose (mg): | Formulation: |
|---|---|---|
| 1 | 0.50 | Rivotril ® IV-injection |
| 2 | 0.50 | 10% GF in 4EG |
| 3 | 0.25 | 10% GF in 4EG |
| 4 | 0.25 | Pure GF |
| 5 | 0.25 | 70% GF in 4EG |
| 6 | 0.25 | Pure 3EG |
| 7 | 0.25 | 5% GF in 4EG |
| 8 | 0.25 | 20% GF in 4EG |
| 9 | 0.25 | 9% EtOH in 4EG |
| 10 | 0.25 | Pure 4EG |
| 11 | 0.25 | 2.5% GF in 4EG[a] |
| 12 | 0.25 | 10% VO in GF |
| 13 | 0.25 | 30% GF in 4EG |
| 14 | 0.25 | 15% GF in 4EG |
| 15 | 0.25 | 7.5% GF in 4EG |
| 16 | 0.25 | 5% Tween in 4EG |
| 17 | 0.25 | 1% GF in 4EG[a] |
| 18 | 0.25 | 5% GF in 4EG[a] |
| 19 | 0.25 | 1% GF in 4EG |
| 20 | 0.25 | 2.5% GF in 4EG |

[a] The drug was applied in 50 µl instead of 100 µl as usual.

FIG. 16 shows a summary of the mean results for test 2 (the rabbit is laying in a supine position) from Table 1–5. The numbers on top of the bars denote the amount of non-responders, within the 10 min. test period, relative to the amount tested (such bars are higher in reality, as only 10 min. are used for non-responders to calculate the mean).

| Vehicle no.: | Dose (mg): | Formulation: |
|---|---|---|
| 1 | 0.50 | Rivotril ® IV-injection |
| 2 | 0.50 | 10% GF in 4EG |
| 3 | 0.25 | 10% GF in 4EG |
| 4 | 0.25 | Pure GF |
| 5 | 0.25 | 70% GF in 4EG |
| 6 | 0.25 | Pure 3EG |
| 7 | 0.25 | 5% GF in 4EG |
| 8 | 0.25 | 20% GF in 4EG |
| 9 | 0.25 | 9% EtOH in 4EG |
| 10 | 0.25 | Pure 4EG |
| 11 | 0.25 | 2.5% GF in 4EG[a] |
| 12 | 0.25 | 10% VO in GF |
| 13 | 0.25 | 30% GF in 4EG |
| 14 | 0.25 | 15% GF in 4EG |
| 15 | 0.25 | 7.5% GF in 4EG |
| 16 | 0.25 | 5% Tween in 4EG |
| 17 | 0.25 | 1% GF in 4EG[a] |
| 18 | 0.25 | 5% GF in 4EG[a] |
| 19 | 0.25 | 1% GF in 4EG |
| 20 | 0.25 | 2.5% GF in 4EG |

[a] The drug was applied in 50 µl instead of 100 µl as usual.

EXAMPLE 15a

Furthermore, the additional compositions stated below were prepared by dissolving the pharmacological active ingredient in the vehicle during sonification and/or gentle hearing. Compositions comprising water are rendered isotonic using sodium chloride and adjusted to a pH in the physiological range of 4.0–7.5 using phosphate buffer.

| Active Ingredient | Unit Dose in mg | Unit Dose in µl | GF % | 4EG % | PEG | H₂O | pH | Example |
|---|---|---|---|---|---|---|---|---|
| Salbutamol | 0.5 | 50 | 10 | | | 90 | | |
| Oxytosin | 5IE | 50 | 5 | | | 95 | | |
| Terbutalin Sulphate | 0.5 | 50 | 1 | | | 99 | | |
| Morphine hydrochlo. | 5 | 100 | 15 | | | 85 | | |
| Beclomet. diproprion | 0.75 | 40 | 5 | 95 | | | | |
| Morphine | 4 | 200 | 20 | 80 | | | | |
| Flunitrazepam | 2 | 150 | 5 | 95 | | | | |
| Aspirin | 100 | 300 | 20 | 80 | | | | |

EXAMPLE 16a

In addition the below compositions were prepared in an analogous manner as described above.

| Active Ingredient | Unit Dose in mg | Unit Dose in µl | GF % | 4EG % | PEG | H₂O | pH | Example |
|---|---|---|---|---|---|---|---|---|
| Aspirin | 300 | 300 | 100 | | | | | |
| Terfenadin | 10 | 300 | | 100 | | | | |
| Beclomethas. diprapionat | 0.75 | 100 | 30 | | | | | 70% veg tab.oi |
| Flunitrazepam | 0.25 | 40 | 30 | | | | | 70% veg tab.oi |

LIST OF REFERENCES

Lau, S. W. J. and Slattery, J. T. (1989), "Absorption of diazepam and lorazepam following intranasal administration." Inernational Journal of Pharmaceutics, 54, 171–174.

Mayer, W., Erbe, S., Wolf, G. and Voigt, R. (1974), "Beiträge zur analytik und staybilität einiger pharmazeutisch interessanter 1.4-benzodiayzepine." Pharmazie 29, H.10–11, 700–707.

Morimoto, K., Tabata, H. and Morisaka, K. (1987), "Nasal absorption of nifedipine from gel preparations in rats." Chemical and Pharmaceutical Bulletins, 35, No. 7, 3041–3044.

Nielsen, N. H., Frolund, L., Bindslev-Jensen, C. and Svendsen, U. G. (1989), "A new formulation of flunisolide for intranasal application reduces side effects." Allergy, 44, 233–234.

Proctor, D. F. (1985), "Nasal physiology in intranasal drug administrations", in Chien, Y. W. (ed.) Transnasal Systemic Medications, Fundamentals, Developmental Concepts and Biomedical Assessments. ELSVIER Science Publishers, Amsterdam 1985, p. 101–105.

Spiegel, A. J. and Noseworthy, M. M. (1983), "Use of nonaqueous solvents in parenteral products". Journal of Pharmaceutical Sciences, October 1963, vol. 52, No. 10, p. 907–927.

Spiegelberg, H., Schläpfer, R., Zbinden, G. and Studer, A. (1956), "Ein neues injizierbares losungsmittel (glycofurol)." Arzneittelforschung, 6, 75–77.

Wilton, N. C. T., Leigh, J., Rosen, D. R. and Pandit, U. A. (1988), "Preanaesthetic sedation of preschool children using intranasal midazolam". Anesthesiology, 69, 972–975.

We claim:

1. A method for administering a therapeutically effective amount of a biologically active substance other than insulin and derivatives thereof to the circulatory system of a mammal comprising administering a pharmaceutical composition having a total volume of 1–1000 µl to a nasal mucosal membrane of the mammal, the pharmaceutical composition comprising the therapeutically effective amount of the biologically active substance dissolved or suspended in a volume of 1–1000 µl of an n-ethylene glycol-containing vehicle comprising at least one n-ethylene glycol represented by the formula II $$H(OCH_2CH_2)_pOH$$

wherein p is from 1 to 8 so that upon administration of the pharmaceutical composition to the nasal mucosal membrane, absorption of the biologically active substance through the mucosal membrane and into the blood stream of the mammal rapidly takes place and thereby allows the biologically active substance to exert its therapeutic effect.

2. The method according to claim 1 wherein the n-ethylene glycol contained in the vehicle is PEG 200.

3. The method according to claim 1 wherein the n-ethylene glycol contained in the vehicle is selected from the group consisting of tri-ethylene glycol and tetra-ethylene glycol.

4. The method according to claim 3 wherein the n-ethylene qlycol is tetra-ethylene glycol.

5. The method according to claim 1 wherein the amount of n-ethylene glycol contained in the vehicle is at least 30 v/v percent.

6. The method according to claim 5 wherein the amount of n-ethylene glycol contained in the vehicle is at least 50 v/v percent.

7. The method according to claim 6 wherein the amount of n-ethylene glycol contained in the vehicle is at least 80 v/v percent.

8. The method according to claim 7 wherein the amount of n-ethylene glycol contained in the vehicle is about 98 v/v percent.

9. The method according to claim 1 wherein the composition comprises the therapeutically effective amount of the biologically active substance dissolved or suspended in a dosage unit quantity volume of 100–300 µL.

10. The method according to claim 9 wherein the composition comprises the therapeutically effective amount of the biologically active substance in the form of a solution or suspension which is administered to the nasal mucosal membrane in a dosage unit quantity volume of 50–150 µl per nostril.

11. The method according to claim 1 wherein the absorption of the biologically active substance through the mucosal membrane and into the blood stream of the mammal results in a peak value ($T_{max}$) of the biologically active substance in the blood of the mammal within a period of 60 minutes upon administration of the substance to the nasal mucosal membrane of the mammal.

12. The method according to claim 11 wherein the absorption of the biologically active substance through the mucosal membrane and into the blood stream of the mammal results in a peak value ($T_{max}$) of the biologically active substance in the blood of the mammal within a period of 30 minutes upon administration of the substance to the nasal mucosal membrane of the mammal.

13. The method according to claim 12 wherein the absorption of the biologically active substance through the mucosal membrane and into the blood stream of the mammal results in a peak value ($T_{max}$) of the biologically active substance in the blood of the mammal within a period of 15 minutes upon administration of the substance to the nasal mucosal membrane of the mammal.

14. The method according to claim 1 wherein the absorption of the biologically active substance through the mucosal membrane and into the blood stream of the mammal results in a maximal therapeutic effect of the biologically active substance within a period of 60 minutes upon administration of the substance to the nasal mucosal membrane of the mammal.

15. The method according to claim 14 wherein the absorption of the biologically active substance through the mucosal membrane and into the blood stream of the mammal results in a maximal therapeutic effect of the biologically active substance within a period of 30 minutes upon administration of the substance to the nasal mucosal membrane of the mammal.

16. The method according to claim 5 wherein the absorption of the biologically active substance through the mucosal membrane and into the blood stream of the mammal results in a maximal therapeutic effect of the biologically active substance within a period of 15 minutes upon administration of the substance to the nasal mucosal membrane of the mammal.

17. The method according to claim 1 wherein the biologically active substance is present in the pharmaceutical composition in a concentration of from 0.0001 to 50 w/v percent.

18. The method according to claim 17 wherein the biologically active substance is present in the pharmaceutical composition in a concentration of from 0.001 to 20 w/v percent.

19. The method according to claim 1 wherein the vehicle further comprises a vegetable oil.

20. The method according to claim 1 wherein the vehicle further comprises nitric acid and/or nitrate in a concentration ranging from 0.0001 to 5 w/v percent.

21. The method according to claim 1 wherein the vehicle is anhydrous.

22. The method according to claim 1 wherein the pharmaceutical composition comprises the biologically active substance in the form of powder, microspheres or liposomes.

23. A method for administering a therapeutically effective amount of insulin or a derivative thereof to the circulatory system of a mammal comprising administering a pharmaceutical composition having a total volume of 1–1000 µl to a nasal mucosal membrane of the mammal, the pharmaceutical composition comprising the therapeutically effective amount of the insulin or the derivative thereof dissolved or suspended in a volume of 1–1000 µl of a n-ethylene glycol-containing anhydrous vehicle comprising at least one n-ethylene glycol represented by the formula II

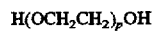

$$H(OCH_2CH_2)_pOH$$

wherein p is from 1 to 8 so that upon administration of the pharmaceutical composition to the nasal mucosal membrane, absorption of the insulin or the derivative thereof through the mucosal membrane and into the blood stream of the mammal rapidly takes place and thereby allows the biologically active substance to exert its therapeutic effect.

24. A method for administering a therapeutically effective amount of insulin or a derivative thereof to the circulatory system of a mammal according to claim 23, wherein the pharmaceutical composition comprising the therapeutically effective amount of the insulin or the derivative thereof has a pH value of about 7.4.

25. The method according to claim 1, wherein the biologically active substance is dissolved in the vehicle.

26. The method according to claim 1, wherein the pharmaceutical composition is liquid.

27. The method according to claim 1, wherein the step of administering the pharmaceutical composition comprises spraying the pharmaceutical composition to the nasal mucosal membrane of the mammal.

28. The method according to claim 23, wherein the biologically active substance is dissolved in the vehicle.

29. The method according to claim 23, wherein the pharmaceutical composition is liquid.

30. The method according to claim 23, wherein the step of administering the pharmaceutical composition comprises spraying the pharmaceutical composition to a nasal mucosal membrane of the mammal.

* * * * *